United States Patent
Kim

(10) Patent No.: US 10,624,603 B2
(45) Date of Patent: Apr. 21, 2020

(54) X-RAY INPUT APPARATUS, X-RAY IMAGING APPARATUS INCLUDING THE SAME, AND METHOD OF CONTROLLING THE X-RAY INPUT APPARATUS

(71) Applicant: Samsung Electronics Co., Ltd., Suwon-si, Gyeonggi-do (KR)

(72) Inventor: Myeong Je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 31 days.

(21) Appl. No.: 16/025,316

(22) Filed: Jul. 2, 2018

(65) Prior Publication Data

US 2019/0000411 A1 Jan. 3, 2019

(30) Foreign Application Priority Data

Jul. 3, 2017 (KR) .................. 10-2017-0084038
Dec. 5, 2017 (KR) .................. 10-2017-0166237

(51) Int. Cl.
*A61B 6/00* (2006.01)

(52) U.S. Cl.
CPC .......... *A61B 6/548* (2013.01); *A61B 6/4464* (2013.01); *A61B 6/4494* (2013.01); *A61B 6/467* (2013.01); *A61B 6/542* (2013.01); *A61B 6/563* (2013.01); *A61B 6/4405* (2013.01)

(58) Field of Classification Search
CPC ..... A61B 6/467; A61B 6/4405; A61B 6/4464; A61B 6/4494; A61B 6/542; A61B 6/548; A61B 6/563; A61B 6/547; A61B 6/56
See application file for complete search history.

(56) References Cited

U.S. PATENT DOCUMENTS

| 5,666,039 A * | 9/1997 | Odaohara | H01M 10/46 320/152 |
| 2009/0143114 A1* | 6/2009 | Vargas | H04W 52/0258 455/574 |
| 2009/0207014 A1* | 8/2009 | Ayed | G08B 13/1427 340/539.13 |
| 2011/0037600 A1* | 2/2011 | Takehara | H01L 31/02021 340/635 |
| 2011/0291800 A1* | 12/2011 | Butzine | A61B 6/544 340/8.1 |

(Continued)

OTHER PUBLICATIONS

European Communication dated Jun. 18, 2019 in European Patent Application No. 18180722.3.

(Continued)

*Primary Examiner* — Chih-Cheng Kao
(74) *Attorney, Agent, or Firm* — Staas & Halsey LLP

(57) ABSTRACT

An X-ray input apparatus includes a body mountable on a holder of an X-ray imaging apparatus, an exposure button provided at an upper portion of the body and configured to receive an X-ray exposure ready command and an X-ray exposure command from a user, an input communicator communicating with the holder via a Bluetooth communication network, and an input controller controlling the input communicator to generate a Bluetooth packet comprising the X-ray exposure ready signal or the X-ray exposure signal and transmit the generated Bluetooth packet to the holder when the X-ray exposure ready command or the X-ray exposure command is input to the exposure button.

19 Claims, 26 Drawing Sheets

(56) References Cited

U.S. PATENT DOCUMENTS

| | | | | |
|---|---|---|---|---|
| 2012/0207273 | A1* | 8/2012 | Kim | A61B 6/4464 |
| | | | | 378/62 |
| 2013/0169429 | A1* | 7/2013 | Zwisler | G08B 13/1427 |
| | | | | 340/531 |
| 2015/0296550 | A1* | 10/2015 | Shelly | H04W 76/14 |
| | | | | 320/108 |
| 2017/0035383 | A1 | 2/2017 | Liu et al. | |

OTHER PUBLICATIONS

Extended European Search Report dated Dec. 4, 2018 in European Patent Application No. 18180722.3.

\* cited by examiner

X-RAY INPUT APPARATUS, X-RAY IMAGING APPARATUS INCLUDING THE SAME, AND METHOD OF CONTROLLING THE X-RAY INPUT APPARATUS

CROSS-REFERENCE TO RELATED APPLICATIONS

This application claims the benefit of Korean Patent Application No. 10-2017-0084038, filed on Jul. 3, 2017 in the Korean Intellectual Property Office, and Korean Patent Application No. 10-2017-0166237, filed on Dec. 5, 2017 in the Korean Intellectual Property Office, the disclosures of which are incorporated herein by reference.

BACKGROUND

1. Field

The following description relates to an X-ray input apparatus controlling X-ray imaging apparatuses, an X-ray imaging apparatus including the same, and a method of controlling the X-ray input apparatus.

2. Description of the Related Art

In medical practice, clinical diagnosis is a major part of treating patients, and the development of medical technology has increased accuracy of the clinical diagnosis and the degree of dependence thereon may further be increased.

Thus, diagnostic imaging apparatuses such as computed tomography (CT) apparatuses, magnetic resonance imaging (MRI) apparatuses, and X-ray imaging apparatuses have become essential equipment for medical practice.

Recently, wireless X-ray input apparatuses have been introduced to conveniently control such diagnostic imaging apparatuses. However, there is a need to increase accuracy of input by an operator in wireless X-ray input apparatuses while the operator carries the X-ray input apparatus.

SUMMARY

Therefore, it is an aspect of the present disclosure to provide an X-ray input apparatus configured to transmit a command input by a user to an X-ray imaging apparatus via a wireless communication network, an X-ray imaging apparatus including the same, and a method of controlling the X-ray input apparatus.

Additional aspects of the disclosure will be set forth in part in the description which follows and, in part, will be obvious from the description, or may be learned by practice of the disclosure.

According to an aspect of an embodiment, an X-ray input apparatus includes a body mountable on a holder of an X-ray imaging apparatus, an exposure button provided at an upper portion of the body and configured to receive an X-ray exposure ready command and an X-ray exposure command from a user, an input communicator communicating with the holder via a Bluetooth communication network, and an input controller controlling the input communicator to generate a Bluetooth packet including the X-ray exposure ready signal or the X-ray exposure signal and transmit the generated Bluetooth packet to the holder when the X-ray exposure ready command or the X-ray exposure command is input to the exposure button.

The input controller may control the input communicator to generate a Bluetooth packet including ID information of the X-ray input apparatus and transmit the generated Bluetooth packet to the holder for paring with the holder.

The input controller may output an anti-theft notification when a distance between the holder and the X-ray input apparatus is maintained beyond a communicable range for a reference time or more.

The X-ray input apparatus may further include a receiver module including a receiving coil in which an AC current is induced by a magnetic field formed by a transmitting coil of the holder and a converter configured to convert the AC current to a DC current, and a battery charged by the DC current.

The input controller may control the input communicator to generate a Bluetooth packet including information on a battery charge status of the X-ray input apparatus and transmits the generated Bluetooth packet to the holder.

The input controller may transmit a battery charge request signal to the holder via the receiving coil or the input communicator when the body is mounted on the holder.

The input controller may transmit a pulse signal including ID information of the X-ray input apparatus to the transmitting coil of the holder via the receiving coil for pairing with the holder.

The input controller may switch an operation mode of the X-ray input apparatus to a sleeping mode when the body is mounted on the holder.

According to an aspect of an embodiment, an X-ray imaging apparatus includes an X-ray source configured to generate X-rays and emit the generated X-rays, a high voltage generator configured to supply a high voltage to the X-ray source, an X-ray input apparatus configured to generate a Bluetooth packet including an X-ray exposure ready signal or an X-ray exposure signal and transmit the generated Bluetooth packet to a holder when the X-ray exposure ready signal or the X-ray exposure signal is input by a user, and the holder on which the X-ray input apparatus is mounted and configured to communicate with the X-ray input apparatus via a Bluetooth communication network.

The X-ray input apparatus may generate a Bluetooth packet including an anti-theft notification and transmits the generated Bluetooth packet to the holder when a distance between the holder and the X-ray input apparatus is maintained beyond a communicable range for a reference time or more.

The X-ray input apparatus may generate a Bluetooth packet including ID information of the X-ray input apparatus and transmits the generated Bluetooth packet to the holder for pairing with the holder.

The X-ray imaging apparatus may further include a transmitting coil provided at the holder and configured to form a magnetic field by a supplied power when the power is supplied from a power supply, a receiving coil in which a current is induced by the magnetic field formed by the transmitting coil, and a battery charged by the current induced in the receiving coil and configured to supply a power to the X-ray input apparatus.

The X-ray input apparatus may generate a Bluetooth packet including information on a battery charge status and transmits the generated Bluetooth packet to the holder.

The holder may control supply and cutoff of the power based on the information on the battery charge status.

The X-ray imaging apparatus may further include an indicator provided at the holder and configured to indicate the information on the battery charge status.

The X-ray input apparatus may transmit a pulse signal including ID information of the X-ray input apparatus to the transmitting coil of the holder via the receiving coil for pairing with the holder.

The X-ray input apparatus may communicate with the holder via a Bluetooth communication network after completion of the pairing with the holder.

The X-ray input apparatus may switch an operation mode to a sleeping mode when mounted on the holder.

The holder may output a notification when the Bluetooth packet including the X-ray exposure signal is not received within a reference time after receiving the Bluetooth packet including the X-ray exposure ready signal.

The holder may output a notification when the Bluetooth packet including the X-ray exposure signal is received before the Bluetooth packet including the X-ray exposure ready signal is received.

According to an aspect of an embodiment, a method of controlling an X-ray input apparatus provided to be mounted on a holder of an X-ray imaging apparatus includes determining whether or not an X-ray exposure ready command or an X-ray exposure command is input to an exposure button provided at the X-ray input apparatus by a user, generating a Bluetooth packet including an X-ray exposure ready signal corresponding to the X-ray exposure ready command or an X-ray exposure signal corresponding to the X-ray exposure command when the X-ray exposure ready command or the X-ray exposure command is input, and transmitting the generated Bluetooth packet to the holder.

The method may further include generating a Bluetooth packet including ID information of the X-ray input apparatus and transmitting the generated Bluetooth packet to the holder for pairing with the holder when the X-ray input apparatus is not paired with the holder.

The method may further include outputting an anti-theft notification when a distance between the holder and the X-ray input apparatus is maintained beyond a communicable range for a reference time or more.

The X-ray input apparatus may include a receiving coil in which a current is induced by a magnetic field formed by a transmitting coil of the holder.

The method may further include transmitting a battery charge request signal to the holder when the X-ray input apparatus is mounted on the holder.

The method may further include transmitting a pulse signal including ID information of the X-ray input apparatus to the transmitting coil of the holder via the receiving coil for pairing with the holder.

The method may further include switching an operation mode of the X-ray input apparatus to a sleeping mode when the body is mounted on the holder.

According to an aspect of an embodiment, an X-ray imaging apparatus includes an X-ray source configured to generate X-rays and emit the generated X-rays, a high voltage generator configured to supply a high voltage to the X-ray source, an X-ray input apparatus configured to receive an X-ray exposure ready command and an X-ray exposure command from a user, a holder on which the X-ray input apparatus is mounted and configured to communicate with the X-ray input apparatus via a Bluetooth communication network, a transmitting coil provided at the holder and configured to form a magnetic field by a supplied power when the power is supplied from a power supply, a receiving coil in which a current is induced by the magnetic field formed by the transmitting coil, and a battery charged by the current induced in the receiving coil and configured to supply a power to the X-ray input apparatus.

The X-ray input apparatus may generate a Bluetooth packet including information on a battery charge status and transmits the generated Bluetooth packet to the holder.

The holder may control supply and cutoff of the power based on the information on the battery charge status.

The X-ray imaging apparatus may further include an indicator provided at the holder and configured to indicate the information on the battery charge status.

The X-ray input apparatus may transmit a pulse signal including ID information of the X-ray input apparatus to the transmitting coil of the holder via the receiving coil for pairing with the holder.

The X-ray input apparatus may communicate with the holder via a Bluetooth communication network after the pairing with the holder is completed.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
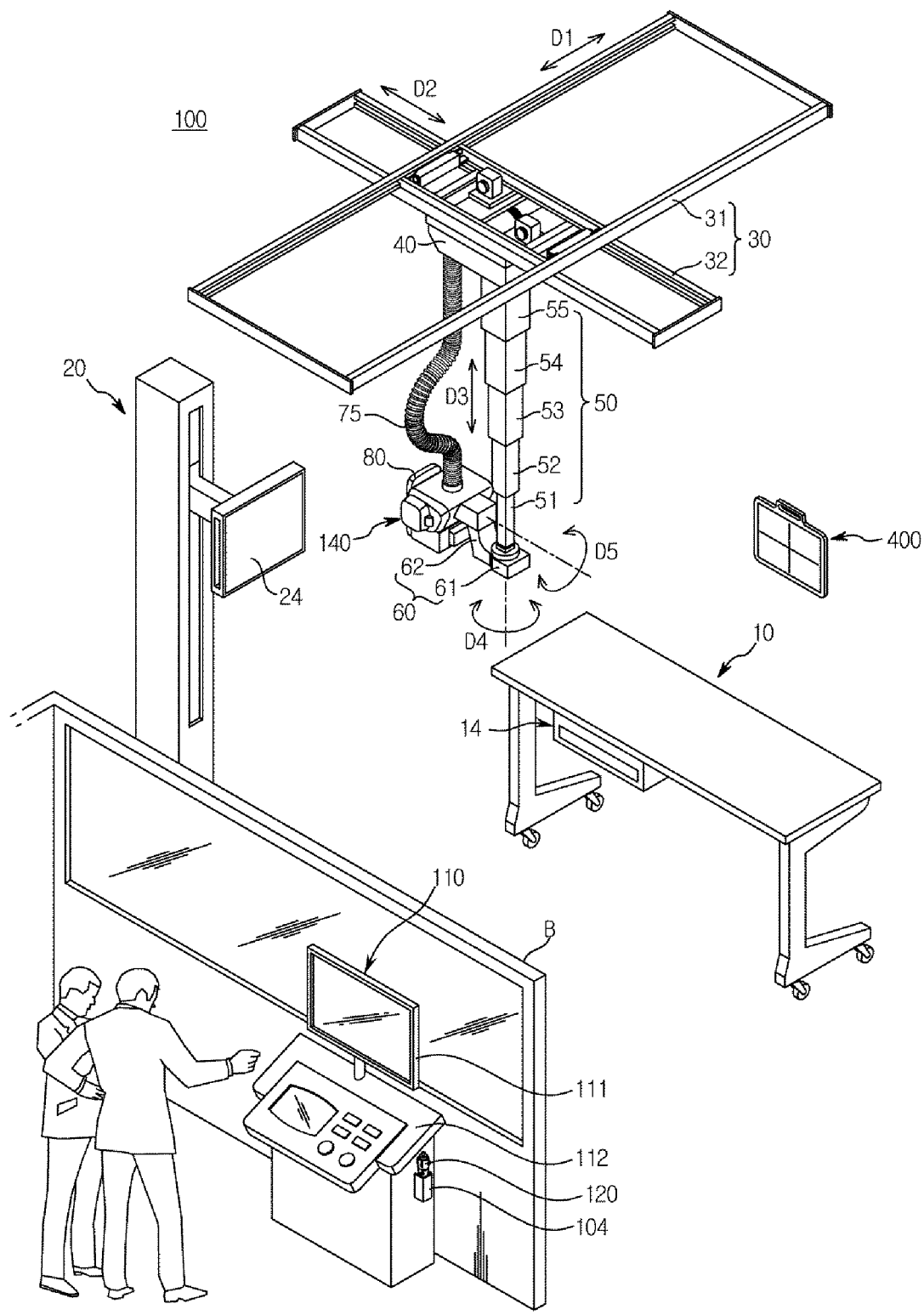
FIG. 1 is a view illustrating an appearance of a conventional X-ray imaging apparatus.

Reference will now be made in detail to the embodiments of the present disclosure, examples of which are illustrated in the accompanying drawings, wherein like reference numerals refer to like elements throughout.

Hereinafter, an X-ray input apparatus, an X-ray imaging apparatus including the same, and a method of controlling the X-ray input apparatus according to embodiments of the present disclosure will be described in detail.

Figure 2:
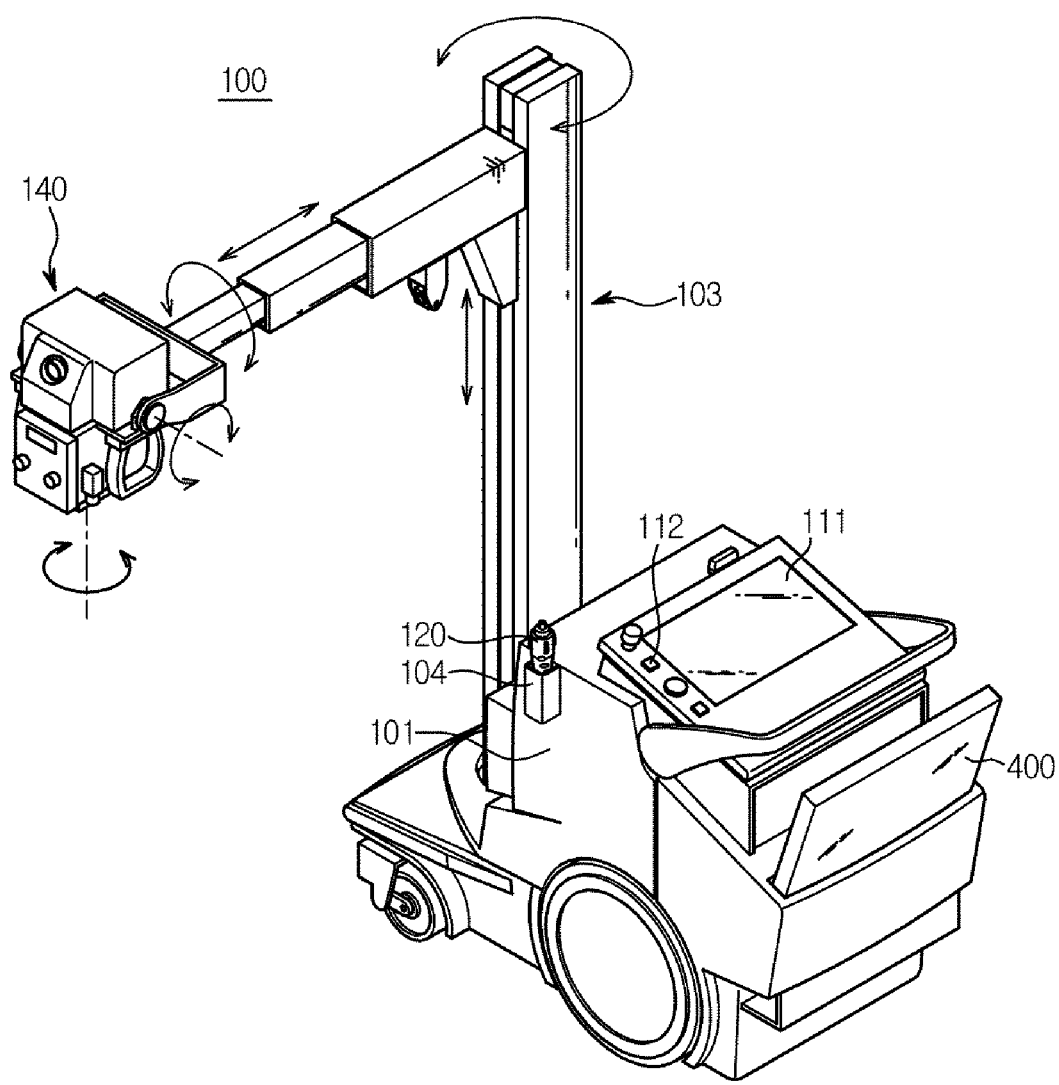
FIG. 2 is a view illustrating an appearance of a mobile X-ray imaging apparatus.

FIGS. 1 and 2 are views illustrating appearances of X-ray imaging apparatuses.

Particularly, FIG. 1 illustrates a ceiling-type X-ray imaging apparatus in which an X-ray source 140 is installed on a ceiling of an examination room as an example of the X-ray imaging apparatus.

Referring to FIG. 1, a guide rail 30 may be installed on the ceiling of the examination room in which an X-ray imaging apparatus 100 is located, and the X-ray source 140 may move to a position corresponding to a target object in a state of being connected to a moving carriage 40 that moves along the guide rail 30.

The guide rail 30 may include a first guide rail 31 and a second guide rail 32 aligned at a predetermined angle. For example, the first guide rail 31 and the second guide rail 32 may be installed to be perpendicular to each other.

The first guide rail 31 may be mounted on the ceiling of the examination room and the second guide rail 32 may be mounted on a lower portion of the first guide rail 31 to be slidably movable.

The moving carriage 40 is arranged at a lower portion of the second guide rail 32 to move along the second guide rail 32. The moving carriage 40 may move in a first direction D1 together with the second guide rail 32 and move in a second direction D2 along the second guide rail 32.

A post frame 50 is connected to a lower portion of the moving carriage 40. The post frame 50 may include a plurality of posts 51, 52, 53, 54, and 55. The plurality of posts 51, 52, 53, 54, and 55 are connected to each other in a foldable manner. Thus, the post frame 50 may shorten in an upward direction of the examination room, i.e., a third direction D3 or extend in a downward direction in a state of being fixed to the moving carriage 40.

Because the X-ray source 140 is connected to the bottom of the post frame 50, a height of the X-ray source 140 from a floor may be adjusted by extending or shortening the post frame 50.

The X-ray source 140 is a device that emits X-rays toward an object and may include an X-ray tube configured to generate X-rays and a collimator configured to adjust an exposure range of the generated X-rays.

The X-ray source 140 may be connected to the moving carriage 40 via a connector 75. Various cables and wires for connecting the X-ray source 140 to other devices may be embedded in the connector 75 and a high voltage generated by a high voltage generator may also be supplied to the X-ray source 140 via the connector 75.

A rotating joint 60 is located between the X-ray source 140 and the post frame 50. The rotating joint 60 may include a first rotating joint 61 connected to the lowest post 51 of the post frame 50 and a second rotating joint 62 connected to the X-ray source 140.

The first rotating joint 61 may rotate in a fourth direction D4 and the second rotating joint 62 may rotate in a fifth direction D5. A tilt angle of the X-ray source 140 may be adjusted by rotating the second rotating joint 62 in the fifth direction D5.

Also, the X-ray source 140 may linearly move in the first direction D1, the second direction D2, and the third direction D3 in a state of being connected to the post frame 50 via the rotating joint 60.

A sub-user interface 80 configured to provide an operator with information and receive a control command from the operator may be provided at one side of the X-ray source 140. In this regard, the operator may be a medical professional obtaining images of the object by using the X-ray imaging apparatus 100, such as a doctor, a radiologist, and a nurse. However, the operator is not limited thereto and may be any person using the X-ray imaging apparatus 100.

Although not shown in the drawings, the sub-user interface 80 may include a display device and an input device. The operator may input a target position of the X-ray source 140 by using the display device and the input device.

The X-ray imaging apparatus 100 may further include a workstation 110 configured to control the overall operation of the X-ray imaging apparatus 100. For example, the workstation 110 may be located in a space separated from a space where the X-ray source 140 is located by a barrier wall B.

The workstation 110 may include a display 111 configured to show an X-ray image, a screen to guide input of a control command, information on various settings related to the X-ray imaging apparatus 100, and the like and an input device 112 configured to receive various control commands related to X-ray imaging from the operator.

The display 111 may include at least one display panel selected from a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel, and an organic light emitting diode (OLED) panel. However, types of the panels included in the display 111 are not limited thereto.

The input device 112 may be implemented using a device such as keyboard, a mouse, a trackball, a jog shuttle, or a touch pad. When the input device 112 is implemented using a touch pad and arranged on a front surface of the display 111, a touch screen may be implemented together with the display 111.

A holder 104 on which an X-ray input apparatus 120 is mounted may be installed at one side of a body of the workstation 110. The operator may mount the X-ray input apparatus 120 on the holder 104 for storage when the X-ray input apparatus 120 is not in use and separate the X-ray input apparatus 120 from the holder 104 to use the X-ray input apparatus 120.

The X-ray input apparatus 120 may be connected to the workstation 110 via a cable. However, a case in which the X-ray input apparatus 120 is connected to the workstation 110 in a wireless manner will be described according to the disclosed embodiment.

A table 10 on which the object lies or sits for radiography may be located at an adjacent position to the X-ray source 140 in a movable range thereof.

The X-ray detector 400 may be mounted on a detector mounting portion 14 of the table 10 or a detector mounting portion 24 of a stand 20. However, radiography may also be performed without mounting the X-ray detector 400 on the table 10 or the stand 20 according to a state of a patient or a target region. In this case, radiography may be performed by emitting X-rays to the target region in a state where the X-ray detector 400 is located behind the target region of the object.

Meanwhile, the X-ray imaging apparatus 100 may also be implemented using a mobile X-ray imaging apparatus as illustrated in FIG. 2. Because the mobile X-ray imaging apparatus includes a movable main body 101 connected to an X-ray source 140 and a movable arm 103 connecting the X-ray source 140 with the main body 101 with various degrees of freedom, the X-ray source 140 may move freely.

A holder 104 on which an X-ray input apparatus 120 is mounted may be installed at one side of the main body 101 of the mobile X-ray imaging apparatus. The operator may mount the X-ray input apparatus 120 on the holder 104 for storage when the X-ray input apparatus 120 is not in use and separate the X-ray input apparatus 120 from the holder 104 to use the X-ray input apparatus 120.

Figure 3:
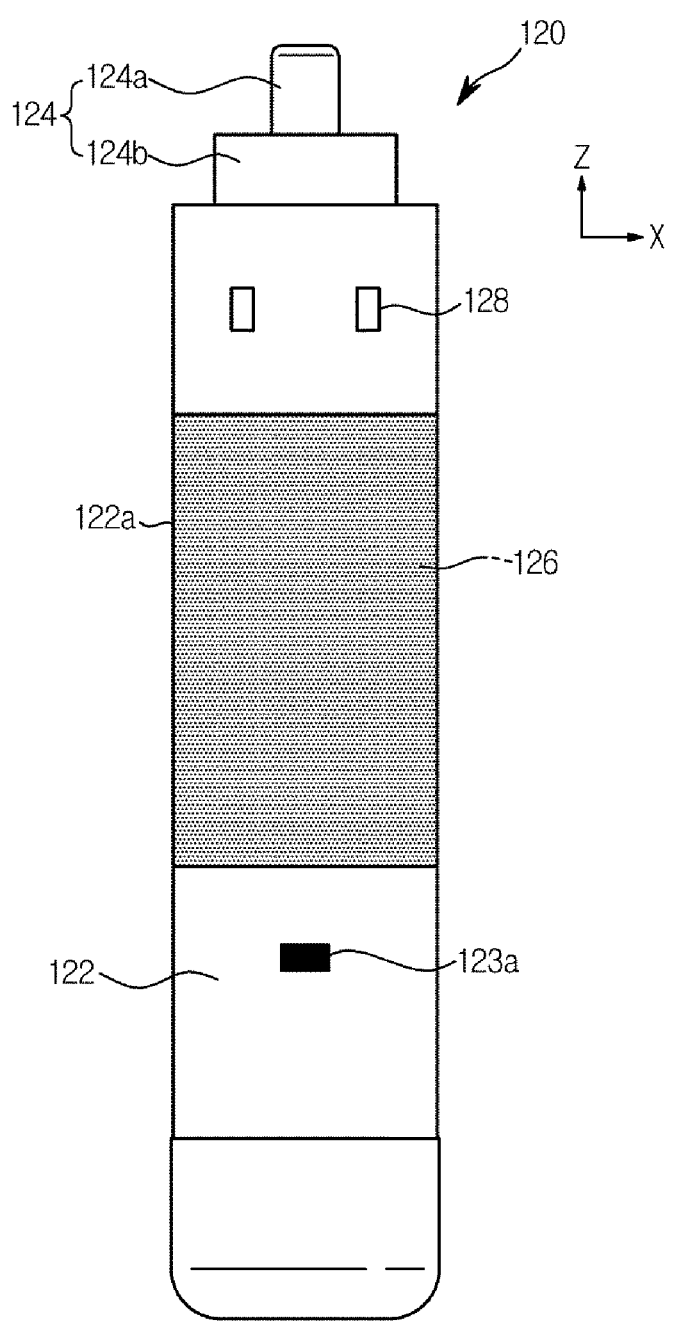
FIG. 3 is a view illustrating one side of an X-ray input apparatus according to an embodiment.
Figure 4:
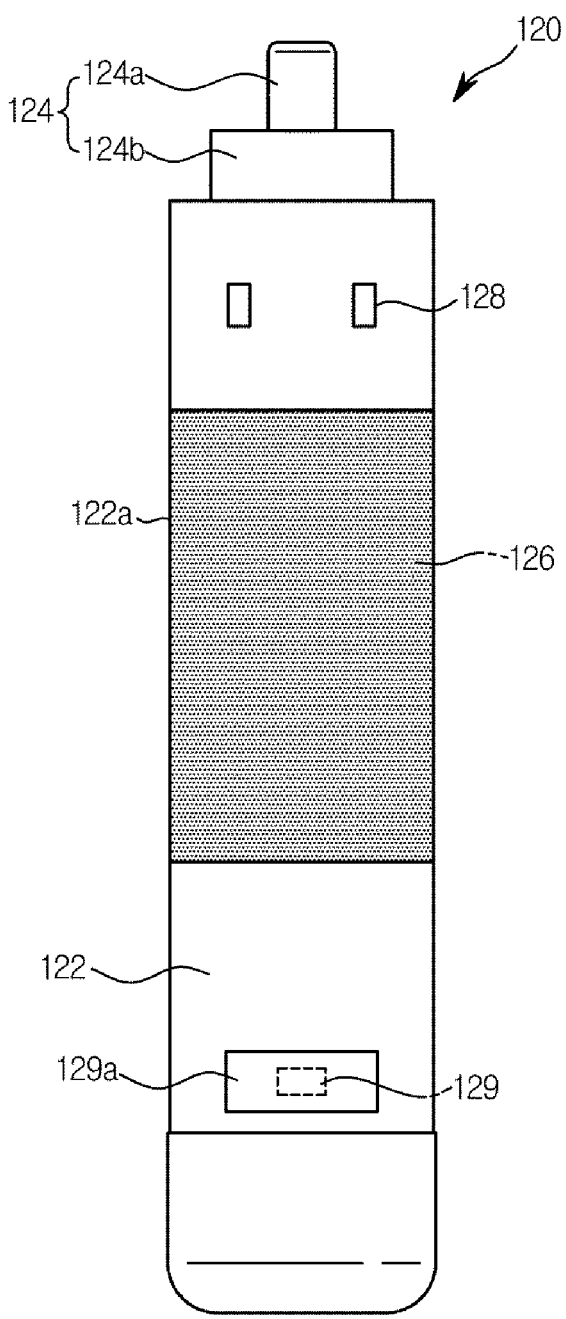
FIG. 4 is a view illustrating the opposite side of the X-ray input apparatus of FIG. 3.
Figure 5:
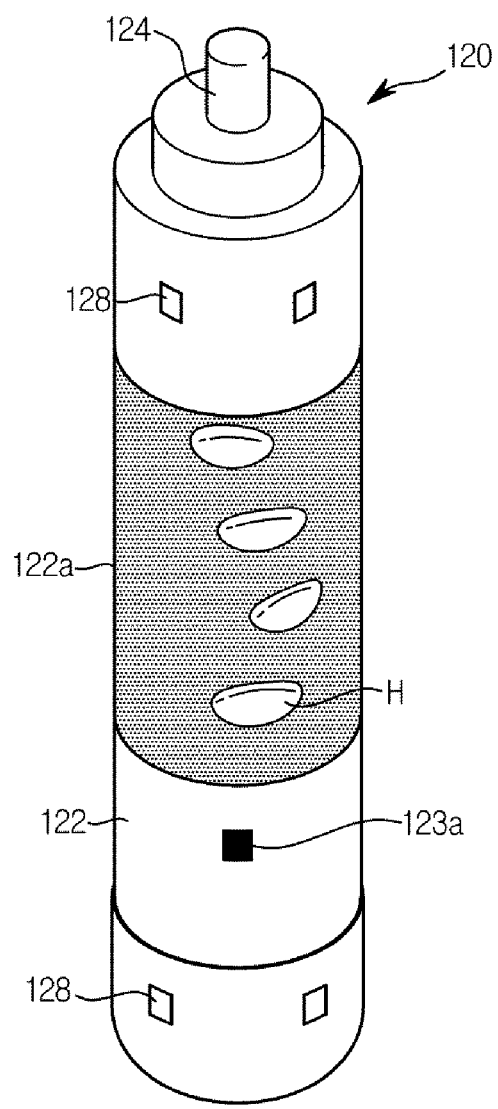
FIG. 5 is a view of an X-ray input apparatus including a hand grip portion according to an embodiment.
Figure 6:
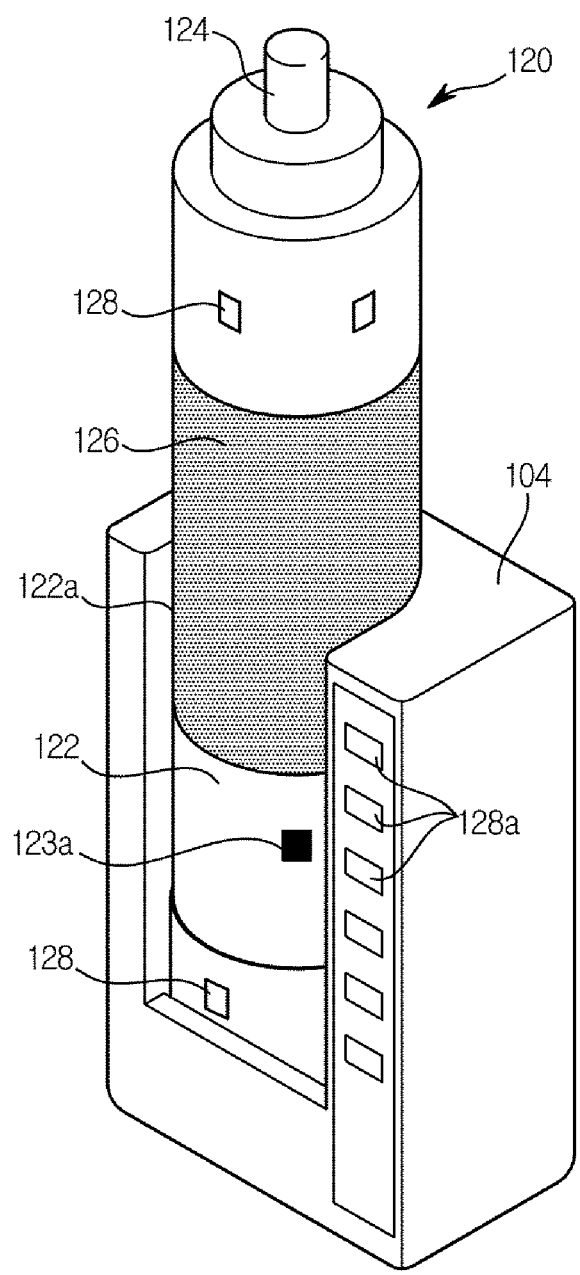
FIG. 6 is a view illustrating the X-ray input apparatus of FIG. 3 installed in a holder provided at a workstation.

FIG. 3 is a view illustrating one side of an X-ray input apparatus according to an embodiment. FIG. 4 is a view illustrating the opposite side of the X-ray input apparatus of FIG. 3. FIG. 5 is a view of an X-ray input apparatus including a hand grip portion according to an embodiment. FIG. 6 is a view illustrating the X-ray input apparatus mounted on a holder.

Referring to FIG. 3, the X-ray input apparatus 120 may include a body 122 on which the holder 104 is mounted, an exposure button 124 located on an upper surface of the body 122 and configured to receive a control command from the operator, a touch sensing device 126 formed on the outer periphery of the body 122, a position sensing device 123a located at one portion of the body 122 and configured to collect position information of the X-ray input apparatus 120, and an indicator 128 located at another portion of the body 122 and configured to provide information on the X-ray input apparatus 120.

Further, as illustrated in FIG. 4, the body 122 of the X-ray input apparatus 120 may be provided with a pairing button 129 configured to pair the X-ray input apparatus 120 with the holder 104 and covered with a cover 129a.

The exposure button 124 may be formed as a two-stage switch protruding from the upper surface of the body 122 to receive input of a ready command (hereinafter, referred to as X-ray exposure ready command) and an exposure command (hereinafter, referred to as X-ray exposure command) from the operator. For example, the exposure button 124 may include a first stage button 124a and a second stage button 124b. The first stage button 124a may be inserted into the second stage button 124b when the ready command is input and the second stage button 124b may be inserted into the body 122 when the exposure command is input.

The X-ray exposure ready command and the X-ray exposure command input via the exposure button 124 may be provided to a process of determining a control command for the X-ray input apparatus 120 or the X-ray imaging apparatus 100 together with touch information input to the touch sensing device 126 or position information collected by the position sensing device 123a. A method of operating the exposure button 124 and the process of determining the control command for the X-ray input apparatus 120 or the X-ray imaging apparatus 100 will be described in more detail below in related parts.

The hand grip portion 122a may be formed on the outer periphery of the body 122. A portion gripped by a user to use the X-ray input apparatus 120, particularly, to operate the exposure button 124 while the X-ray input apparatus 120 is carried by the user, may be referred to as the hand grip portion 122a. For example, the hand grip portion 122a may be located at the center of the body 122 in a Z-axis direction and at a closer position to the exposure button 124.

The hand grip portion 122a may have finger-shaped engraved patterns H allowing the operator to easily grip the X-ray input apparatus 120 as illustrated in FIG. 5. In addition, the engraved patterns H may guide the operator to grip the X-ray input apparatus 120 at appropriate positions.

The touch sensing device 126 may include a touch sensor and the touch sensor may operate as a capacitance sensor.

The touch sensing device 126 may be located on the outer periphery, particularly, at the hand grip portion 122a, of the body 122. As the touch sensing device 126, one touch sensor may be arranged to surround the outer periphery of the body 122 or a plurality of touch sensors may be arranged to be spaced apart from each other at predetermined intervals. For example, when 4 touch sensors are used, the touch sensors may be arranged to be spaced apart from each other at 90° intervals with respect to a central axis penetrating the center of the body 122.

The position of the touch sensing device 126 is not particularly limited so long as the touch sensing device 126 is located at an area in contact with the operator when the X-ray input apparatus 120 is gripped by the operator.

The hand grip portion 122a may be provided on the outer surface of the body 122 to protect the touch sensing device 126 from an external stimulus. In addition, the hand grip portion 122a may sense a touch of the operator immediately after the X-ray input apparatus 120 is gripped by the operator. Thus, when the touch sensing device 126 senses a touch, the X-ray input apparatus 120 may determine that the X-ray input apparatus 120 is gripped by the operator.

The position sensing device 123a is provided at one side of the body 122. The position sensing device 123a is a component to collect information on whether or not the X-ray input apparatus 120 is mounted on the holder 104 and may be installed at a position in which information on a relative position of the X-ray input apparatus 120 to the holder 104 is easily collected. For example, the position sensing device 123a may be installed at a lower end of one side of the body 122. However, the installation position of the position sensing device 123a is not limited thereto and the position sensing device 123a may be installed at any position where position information of the X-ray input apparatus 120 is easily collected.

The position sensing device 123a may include at least one type of a magnetic field sensor, a limit switch, an optical sensor, and an ultrasound sensor. For example, when the position sensing device 123a includes a magnetic field sensor, a magnet may be provided at a position of the holder 104 corresponding to the position sensing device 123a.

Also, when the position sensing device 123a includes an optical sensor or an ultrasound sensor, the position sensing device 123a may include a transmitter configured to emit light such as infrared light and visible light and ultrasound and a receiver configured to receive light or ultrasound reflected by an inner wall of the holder 104. Alternatively, the receiver may be installed at the X-ray input apparatus 120 and the transmitter may be installed at the holder 104.

However, types of available position sensing device 123a are not limited to the above described examples.

The indicator 128 configured to provide information on the X-ray input apparatus 120 or the X-ray imaging apparatus 100 may be provided at one side of the body 122. For example, the indicator 128 may be provided at an upper end or a lower end of one side of the X-ray input apparatus 120.

The indicator 128 may include a visual indicator configured to provide a state of the X-ray input apparatus 120 by a visual method and an audible indicator configured to provide the state of the X-ray input apparatus 120 by an audible method. According to the present embodiment, the visual indicator may be provided as an LED light source and the audible indicator may be provided as a speaker.

For example, the LED light source may emit yellow light while the X-ray imaging apparatus 100 is ready for X-ray exposure, green light while the X-ray imaging apparatus 100 is emitting X-rays, and red light while the X-ray imaging apparatus 100 is controlling a collimator. In this case, the colors of light emitted by the LED light source are not limited thereto and various other colors of light may be provided by the indicator 128 according to a designer's intention.

As another example, the LED light source may indicate battery information of the X-ray input apparatus 120. Specifically, the LED light source may emit green light when a battery of the X-ray input apparatus 120 is charged 100%, yellow light when the battery is charged to a predetermined reference level or more, and red light when the battery is charged to a level less than the predetermined reference level. In this regard, the colors of the light emitted from the LED light source are not limited thereto and various other colors of light may be provided by the indicators according to a designer's intention.

In addition, when the X-ray input apparatus 120 is far away from the holder 104 by a predetermined distance or more, the speaker may provide an audible feedback, i.e., an audible notification to prevent loss of the X-ray input apparatus 120.

Alternatively, a speaker may provide an audible feedback when the X-ray input apparatus 120 is separated from the holder 104 over a predetermined time regardless of distance. According to an embodiment, the audible feedback may be provided to the operator in a different manner according to the situation. According to the embodiment, the mobile X-ray input apparatus 120 may not be lost or stolen by providing various audible feedbacks through the speaker under certain circumstances.

As described above, the pairing button 129 may be provided on the back surface of the body 122 in a state of being protected by the cover 129a. The pairing button 129 is a button to pair the holder 104 of the X-ray imaging apparatus 100 with the X-ray input apparatus 120 before using the X-ray imaging apparatus 100 and the X-ray input apparatus 120. Because this button is not used after pairing the devices, the pairing button 129 may be provided in a state of being protected by the cover 129a.

As illustrated in FIG. 6, an indicator 128a configured to provide information on the X-ray input apparatus 120 paired with the X-ray imaging apparatus 100 may be provided at a body of the holder 104. For example, the indicator 128a may be located at a front surface or a side surface of the body of the holder 104 and may include a visual indicator configured to provide a state of the X-ray input apparatus 120 by a visual method and an audible indicator configured to provide the state of the X-ray input apparatus 120 by an audible method. According to the present embodiment, the visual indicator may be provided as an LED light source and the audible indicator may be provided as a speaker.

For example, the indicator 128a may indicate On/Off information of the X-ray input apparatus 120, battery information (information on battery charge state), On/Off information of a touch sensor of the touch sensing device 126 and the like using an LED light source. According to an embodiment, the indicator 128a may indicate information on a communication state between the X-ray input apparatus 120 and the X-ray imaging apparatus 100.

As another example, the speaker of the indicator 128a may provide an audible feedback when the X-ray input apparatus 120 is far away from the holder 104 at a predetermined distance or more or when the X-ray input apparatus 120 is separated from the holder 104 over a predetermined time.

Next, a method of inputting a control command to the X-ray input apparatus 120 having the above-described structure will be described.

Figure 7:
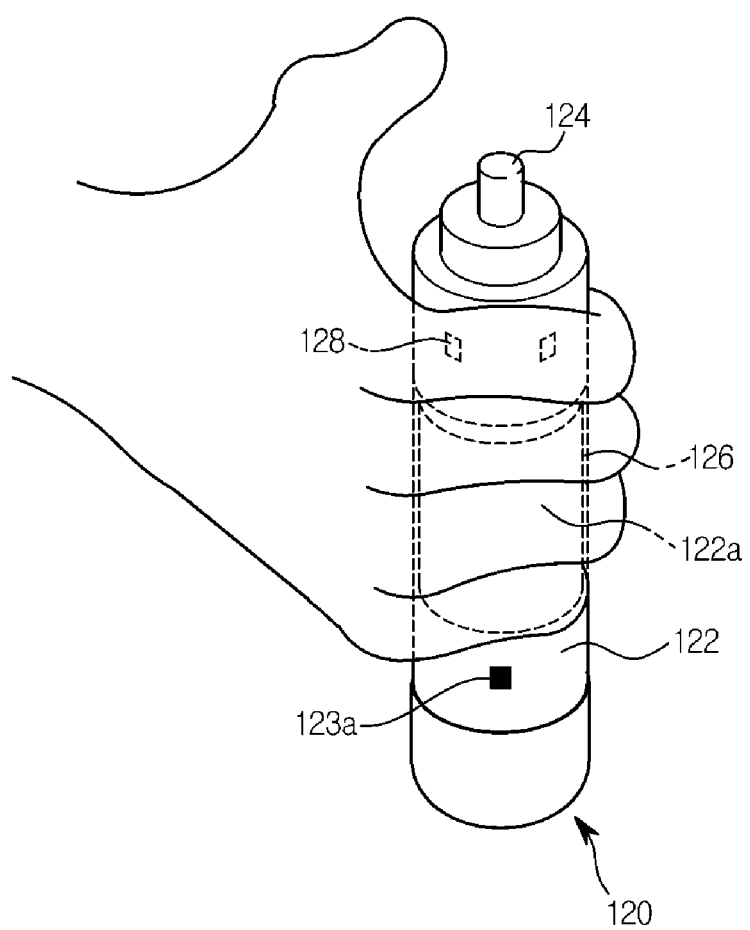
FIGS. 7, 8, and 9 are views for describing a method of inputting a control command to the X-ray input apparatus.
Figure 8:
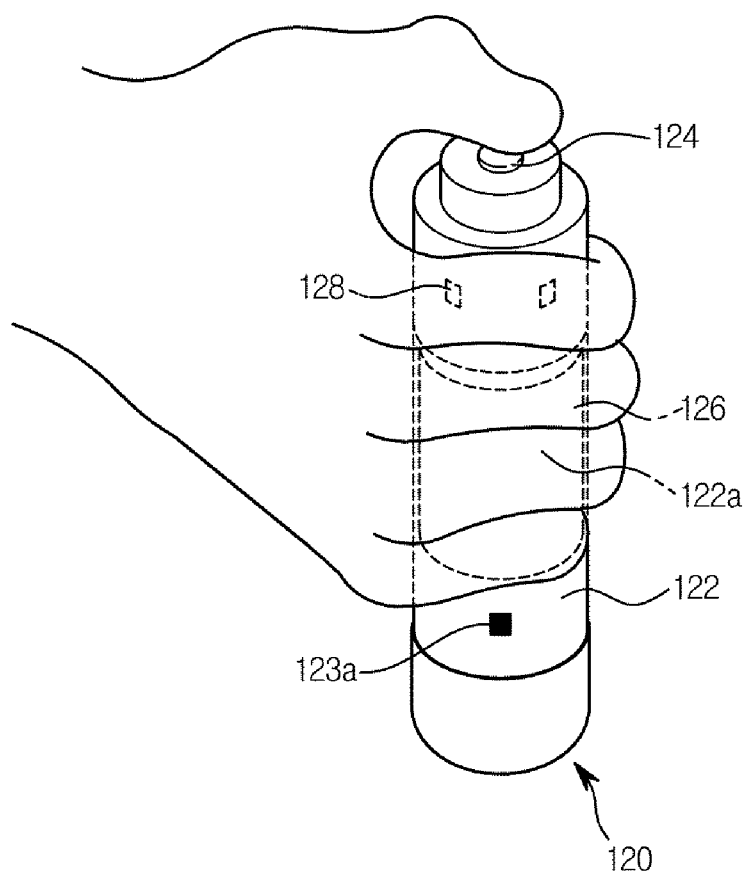
Figure 9:
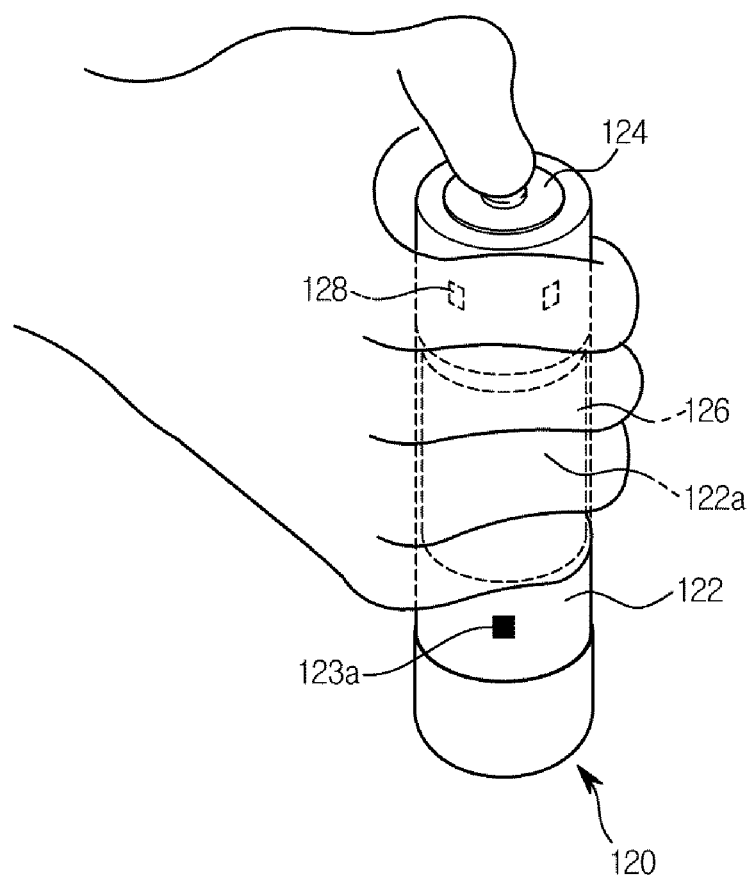

FIGS. 7 to 9 are views for describing a method of inputting a control command to an X-ray input apparatus.

FIGS. 7 to 9 illustrate a method of inputting a control command by applying a pressure to the exposure button 124 protruding from the upper surface of the body 122 while the X-ray input apparatus 120 is gripped on the hand grip portion 122a of the X-ray input apparatus 120.

As illustrated in FIG. 7, the operator may grip the X-ray input apparatus 120 on the hand grip portion 122a. For example, the operator may grip the hand grip portion 122a with four fingers except for a thumb. When the hand grip portion 122a is gripped as described above, the touch sensing device 126 may detect a touch of the operator. The operator may input the control command by applying a pressure to the exposure button 124 protruding from the upper surface of the body 122 using the thumb in a state of touching the touch sensing device 126 using the other four fingers.

As illustrated in FIG. 8, the operator may input an X-ray exposure ready command for preheating by gripping the hand grip portion 122a and locating the exposure button 124 at a ready position in a state where the touch sensing device 126 detects a touch of the operator. Specifically, the operator may input a predetermined first command by applying a pressure of a first critical pressure or more to less than a second critical pressure to the first stage button 124a. Here, the predetermined first command may include the X-ray exposure ready command. In this case, the entire or a part of the first stage button 124a may be inserted into the second stage button 124b.

When the X-ray exposure ready command is input, the LED light source of the indicator 128 may emit yellow light. Hereinafter, descriptions given above will not be repeated.

Next, as illustrated in FIG. 9, an X-ray exposure command is input by further applying an additional pressure to the exposure button 124 in a state where the touch sensing device 126 detects the touch of the operator and the exposure button 124 is in the ready state. For example, the operator may apply a pressure of the second critical pressure or more to the exposure button 124 to input a predetermined second command. Here, the predetermined second command may include the X-ray exposure command. In this case, the entire or a part of the second stage button 124b may be inserted into the body 122.

The first critical pressure may be the same as or smaller than the second critical pressure. That is, the X-ray exposure command may be input by continuously applying the same pressure after the X-ray exposure ready command is input by inserting the first stage button 124*a* into the second stage button 124*b*. Alternatively, the X-ray exposure command may be input by applying a greater pressure than that applied to input the X-ray exposure ready command.

In either case, the X-ray exposure command may be input after the X-ray exposure ready command is input. That is, X-rays may be emitted after the X-ray exposure ready command is input.

When the X-ray exposure command is input, the LED light source of the indicator 128 may emit green light. Hereinafter, descriptions given above will not be repeated.

The method of inputting the X-ray exposure ready command and the X-ray exposure command has been described above based on the touch sensing device 126 and the exposure button 124 of the X-ray input apparatus 120. Meanwhile, the method of inputting the X-ray exposure ready command and the X-ray exposure command is not limited thereto. According to an embodiment, the X-ray exposure ready command and the X-ray exposure command may also be input by recognizing a speech of the operator via a microphone provided in the X-ray input apparatus 120.

Next, the operation of the X-ray input apparatus 120 and the X-ray imaging apparatus 100 including the same will be described based on the above descriptions.

Figure 10:
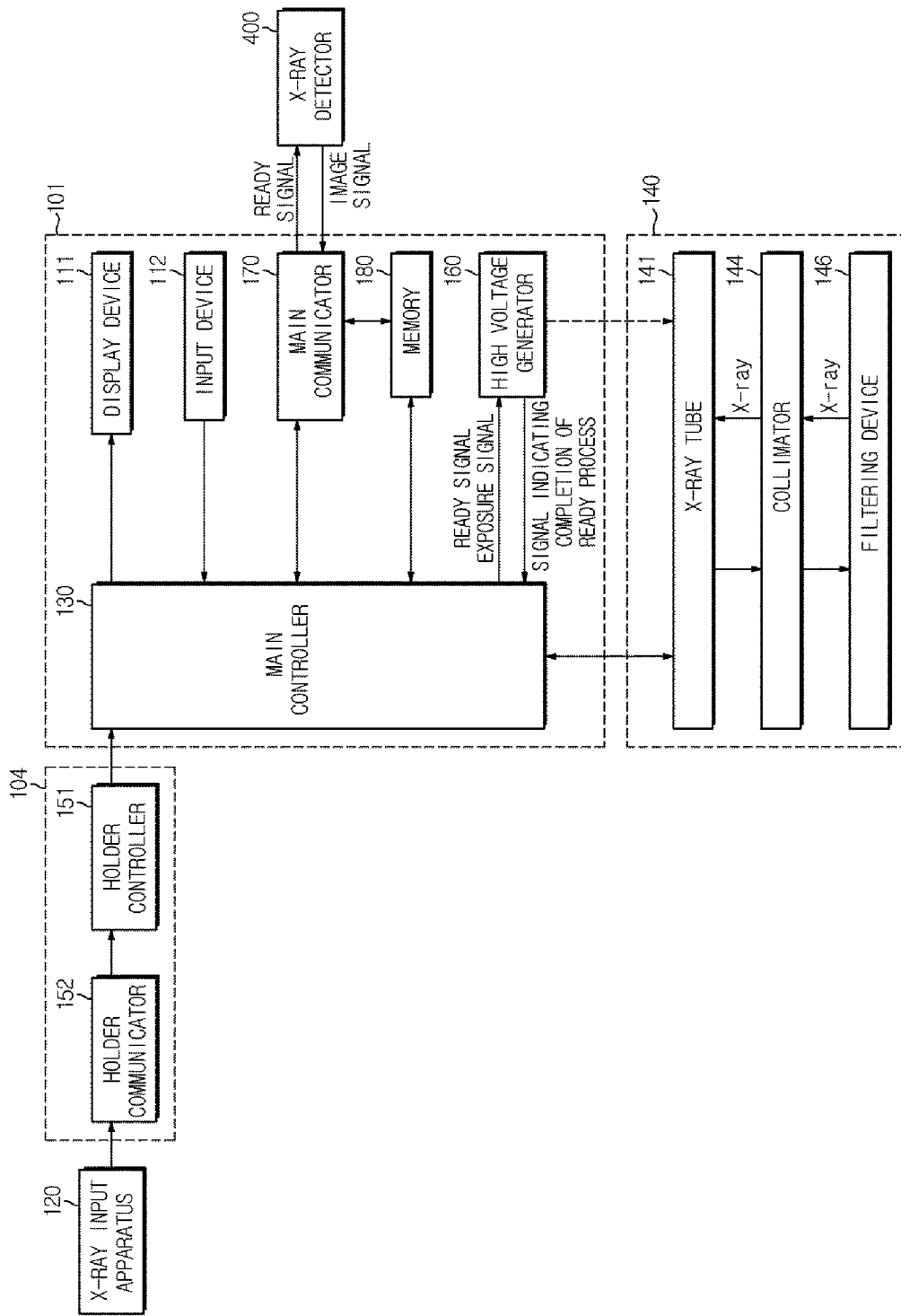
FIG. 10 is a control block diagram of an X-ray imaging apparatus according to an embodiment.
Figure 11:
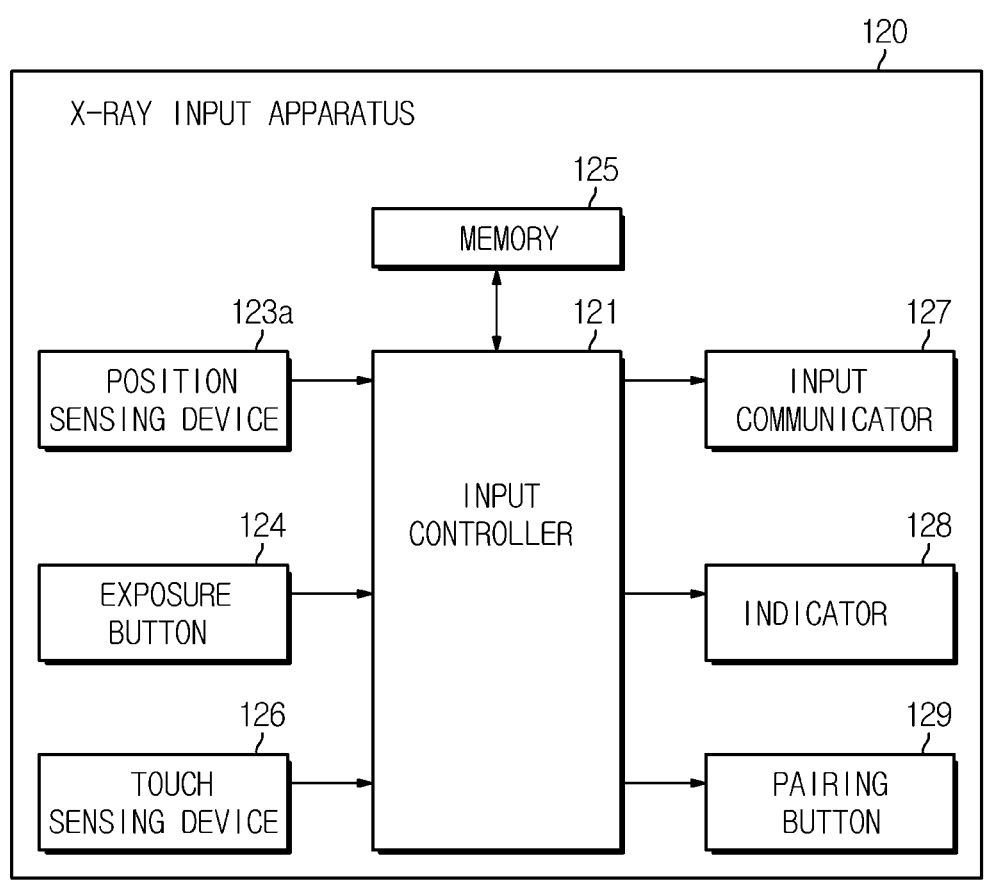
FIG. 11 is a control block diagram of an X-ray input apparatus according to an embodiment.

FIG. 10 is a control block diagram of an X-ray imaging apparatus according to an embodiment. FIG. 11 is a control block diagram of an X-ray input apparatus according to an embodiment.

Referring to FIG. 10, the X-ray imaging apparatus 100 includes the X-ray input apparatus 120 configured to receive a command to control the X-ray imaging apparatus 100 from the operator, a holder communicator 152 provided in the holder 104 and configured to receive a signal from the X-ray input apparatus 120, a holder controller 151 configured to convert the signal received from the X-ray input apparatus 120 into a form that may be processed by the X-ray imaging apparatus 100, a main controller 130 configured to control the overall operation of the X-ray imaging apparatus 100, the X-ray source 140 configured to generate and emit X-rays, a high voltage generator 160 configured to apply high voltage energy to the X-ray source 140, a main communicator 170 configured to communicate with the X-ray detector 400, a memory 180, a display device 111 configured to display an X-ray image, and an input device 112 configured to receive a command of the user.

The X-ray source 140 may include an X-ray tube 141 configured to generate X-rays upon receiving the high voltage energy generated by the high voltage generator 160 and emit the X-rays and a collimator 144 configured to guide a path of X-rays emitted by the X-ray tube 141.

The X-ray source 140 may further include a filtering device 146 configured to adjust an amount of X-rays emitted by the X-ray tube 141.

Referring to FIG. 11, the X-ray input apparatus 120 includes a position sensing device 123*a* configured to detect a position of the X-ray input apparatus 120, a touch sensing device 126 configured to detect a touch, an exposure button 124 configured to receive input of an X-ray exposure command or an X-ray exposure ready command from the user, an input controller 121 configured to control the operation of the X-ray input apparatus 120, an input communicator 127 configured to transmit/receive a signal to/from the holder 104, a memory 125 storing information collected by the position sensing device 123*a* or the touch sensing device 126, an indicator 128 configured to indicate a state of the X-ray input apparatus 120, and a pairing button 129 configured to receive a pairing command.

As described above, the exposure button 124 is configured to receive input of a control command to control the X-ray imaging apparatus 100 from the operator. The exposure button 124 is provided as a two-stage switch as described above. When a pressure of the first critical pressure or more to less than the second critical pressure is applied to the exposure button 124, a first signal is output. When a pressure of the second critical pressure or more is applied thereto, a second signal is output.

The first signal may be determined as the X-ray exposure ready signal based on touch signal value information generated by the touch sensing device 126 and may be provided to a process of generating a calibration control signal of the touch sensing device 126 together with the sensor value information generated by the position sensing device 123*a*. In addition, the second signal may be determined as the X-ray exposure signal based on touch signal value information generated by the touch sensing device 126.

The position sensing device 123*a* collects position information of the X-ray input apparatus 120. More particularly, the position sensing device 123*a* collects information on whether the X-ray input apparatus 120 is mounted on the holder 104. The sensor value information collected by the position sensing device 123*a* is transmitted to the input controller 121 to be used for determination of whether or not the body 122 of the X-ray input apparatus 120 is mounted on the holder 104.

The memory 125 may temporarily or non-temporarily store sensor value information collected by the position sensing device 123*a*, touch input value information sensed by the touch sensing device 126, signal information received from the exposure button 124, reference values used in various determination processes, and the like.

The memory 125 may include high-speed random access memory, magnetic disk, static random access memory (SRAM), dynamic random access memory (DRAM), or read-only memory (ROM), without being limited thereto.

The memory 125 may be detachable from the X-ray input apparatus 120. For example, the memory 125 may include a compact flash (CF) card, a secure digital (SD) card, a smart media (SM) card, a multimedia card (MMC), or a memory stick, but types of the memory 125 are not limited thereto.

The input communicator 127 may transmit signal information generated by the X-ray input apparatus 120 to the holder communicator 152 provided in the holder 104.

The input communicator 127 may include at least one of a wireless LAN and a short-range communication unit corresponding to performance and structure of the X-ray input apparatus 120. Although the wireless LAN or the short-rang communication unit are used as a first communicator 123 of the mobile X-ray input apparatus 120 according to an embodiment, a wired Ethernet may also be in the case where a wired X-ray input apparatus 120 is used.

A wireless LAN module may support a wireless LAN standard (IEEE1002.11x) of The Institute of Electrical and Electronics Engineers (IEEE).

Short-range communication of the short-range communication unit may include Bluetooth, Bluetooth low energy, Zigbee communication, infrared data association (IrDA), Wi-Fi, Ultra Wideband (UWB), and Near Field Communication (NFC). However, the short-range communication is not limited thereto but may be implemented using various forms well known in the art.

However, in the following embodiment, Bluetooth will be described as an example of communication between the input communicator 127 and the holder 104 for detailed descriptions thereof.

The input controller 121 controls the overall operation of the X-ray input apparatus 120. The input controller 121 determines an operation to be performed by the X-ray input apparatus 120 based on first signal information and second signal information generated by the exposure button 124, touch signal information generated by the touch sensing device 126, and sensor value information generated by the position sensing device 123a. Hereinafter, a process of determining the operation to be performed by the X-ray input apparatus 120, the determination performed by the input controller 121, will be exemplarily described.

First, the input controller 121 may determine whether or not the X-ray input apparatus 120 is mounted on the holder 104 based on the sensor value information received from the position sensing device 123a. For example, a reference value indicating that the body 122 is mounted on the holder 104 may be pre-stored according to types of the position sensing device 123a. The pre-stored reference value may be in a predetermined range. The input controller 121 may determine whether or not the body 122 is mounted on the holder 104 by comparing an output of the position sensing device 123a with the pre-stored reference value.

Upon determination that the body 122 is mounted on the holder 104, the input controller 121 may perform an operation for pairing unless the X-ray input apparatus 120 and the holder 104 are not paired. In addition, according to an embodiment, when a pairing command is input by the user via the pairing button 129, the pairing operation may be performed. Detailed description of the pairing operation will be given below.

In addition, upon determination that the body 122 is mounted on the holder 104, the input controller 121 may also perform operations of charging a battery and controlling calibration.

In addition, upon determination that the body 122 is mounted on the holder 104, the input controller 121 may switch an operation mode of the X-ray input apparatus 120 to a sleeping mode or a waiting mode. Because the sleeping mode or the waiting mode according to the embodiment may refer to modes of reducing consumption of the battery by turning off components except for the position sensing device 123a and a circuit used to determine a position. However, according to an embodiment, components turned off during the sleeping mode or the waiting mode may also be set in a different way.

When an output of the touch sensing device 126 is a capacitance threshold or less, i.e., when a touch of the operator is detected, and the input controller 121 receives the first signal or the second signal from the exposure button 124, the input controller 121 may transmit the X-ray exposure ready signal or the X-ray exposure signal to the holder communicator 152 via the input communicator 127.

The input controller 121 transmits the X-ray exposure ready signal or the X-ray exposure signal in a wireless communication method as described above. To this end, the input controller 121 may encode the X-ray exposure ready signal or the X-ray exposure signal into a predetermined standard form according to the wireless communication method.

For example, when the input communicator 127 includes a Bluetooth communication module, the input controller 121 or the input communicator 127 may generate a Bluetooth packet including the X-ray exposure ready signal or the X-ray exposure signal.

The input communicator 127 transmits the generated Bluetooth packet to the holder communicator 152. The holder communicator 152 is provided to communicate with the X-ray input apparatus 120 and may include a communication module corresponding to the input communicator 127. For example, when the input communicator 127 includes a Bluetooth communication module, the holder communicator 152 may also include a Bluetooth communication module.

The holder controller 151 may decode a signal in the packet form received from the X-ray input apparatus 120 into a form that may be processed by the main controller 130 of the X-ray imaging apparatus 100. For example, because the holder controller 151 performs a process opposite to that of generating the packet of the signal performed by the input controller 121 or the input communicator 127 of the X-ray input apparatus 120, the received signal in the packet form may be converted into a form recognized by the main controller 130. Alternatively, a processor included in the holder communicator 152 may perform the afore-mentioned decoding process.

As described above, the X-ray input apparatus 120 may be provided with the pairing button 129. The X-ray imaging apparatus 100 and the X-ray input apparatus 120 may be paired with each other during the initial setting process of the X-ray input apparatus 120 such that the X-ray imaging apparatus 100 and the X-ray input apparatus 120 may communicate with each other.

When the operator inputs the pairing command via the pairing button 129, the input communicator 127 of the X-ray input apparatus 120 transmits a packet including ID information of the X-ray input apparatus 120 to the holder 104 so that the X-ray input apparatus 120 and the holder 104 are paired.

Meanwhile, the X-ray input apparatus 120 may not be provided with the pairing button 129. In this case, the X-ray input apparatus 120 may be paired with the holder 104 according to the following method.

For example, when the X-ray input apparatus 120 is mounted on the holder 104, the input communicator 127 of the X-ray input apparatus 120 transmits a pairing request signal to the holder 104 for pairing with the holder 104. Particularly, the input controller 121 may determine whether or not the X-ray input apparatus 120 is mounted on the holder 104 based on the output of the position sensing device 123a. Upon determination that the X-ray input apparatus 120 is mounted on the holder 104, the input controller 121 may transmit the pairing request signal to the holder 104 by controlling the input communicator 127 although a pairing command is not separately input via the pairing button 129. In this case, pairing of devices may be performed more simply by pairing the X-ray input apparatus 120 with the holder 104 on which the X-ray input apparatus 120 is mounted in the case where the X-ray input apparatus 120 is mounted on the holder 104.

Figure 12:
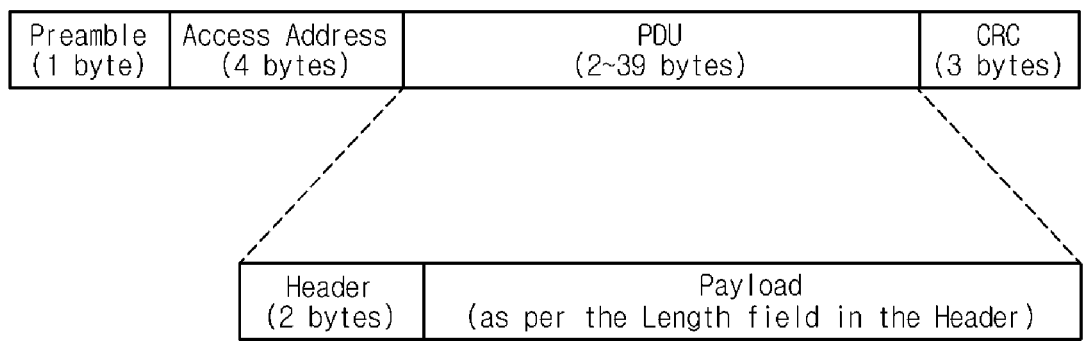
FIG. 12 is a diagram exemplarily illustrating a packet structure used for communication between an X-ray input apparatus and an X-ray imaging apparatus according to an embodiment.

FIG. 12 is a diagram exemplarily illustrating a packet structure used for communication between an X-ray input apparatus and an X-ray imaging apparatus according to an embodiment.

For example, a Bluetooth packet may include an advertising packet used for pairing and a data packet used for transmission and reception of signals after pairing. The advertising packet may be transmitted via an advertising channel and the data packet may be transmitted/received via a data channel.

The advertising packet and the data packet may have a basic Bluetooth packet structure and may have different information arranged to packet data units (PDUs).

Referring to FIG. 12, a Bluetooth packet may include Preamble, Access Address, Cyclical Redundancy Check (CRC), and Packet Data Unit (PDU). The Preamble is a field indicating the start of the packet and may have a size of 1 byte and may be used for synchronization during frequency hopping or protocol management.

The Access Address is a field indicating an address for accessing a packet and may have a size of 4 bytes. Because the advertising is one-way communication, an address for accessing the advertising packet is unnecessary so as to be fixed to a predetermined value. The Access Address of the data packet may be determined randomly.

The CRC is a field for storing a check value to detect an error in data transmission.

The PDU is a space to store data and may be divided into a Header and a Payload. Basic information for data may be stored in the Header and main data may be stored in the Payload.

Before the X-ray input apparatus 120 is paired with the holder 104 of the X-ray imaging apparatus 100, the holder communicator 152 may broadcast the advertising packet having the structure illustrated in FIG. 12.

For example, the PDU may have fields of Sequence Number (SEQ) as a number indicating the order of a packet, Source Address (SRC) indicating an address of a source device, Destination Address indicating an address of a destination device, Operation Code (OP) as a field indicating a meaning of a message, and the like.

The holder 104 may transmit an advertising signal prepared by adding ID information such as MAC address to the PDU.

When the pairing command is input via the pairing button 129 of the X-ray input apparatus 120 or when the X-ray input apparatus 120 is mounted on the holder 104, the input controller 121 may read the advertising packet by scanning and transmit the pairing request signal to the holder 104.

The pairing request signal may also have the Bluetooth packet structure as illustrated in FIG. 12 and the input communicator 127 may transmit the pairing request signal by adding ID information thereof to the Bluetooth packet.

When the holder 104 transmits a response signal to the X-ray input apparatus 120 in response to the received pairing request signal, pairing of the X-ray input apparatus 120 with the holder 104 is completed so that the X-ray input apparatus 120 and the holder 104 may communicate with each other.

When the pairing of the holder 104 with the X-ray input apparatus 120 is completed, the X-ray input apparatus 120 may transmit the Bluetooth packet including the X-ray exposure ready signal and the X-ray exposure signal to the holder 104.

In addition, the X-ray input apparatus 120 may transmit the Bluetooth packet including an On/Off signal of a lamp of the collimator 144 to the holder 104.

Meanwhile, a packet may be lost due to a network error or the like in a process of exchanging signals between the X-ray input apparatus 120 and the holder 104.

For example, when the X-ray exposure signal is not received within a predetermined reference time even after the X-ray exposure ready signal is received from the X-ray input apparatus 120, the holder controller 151 may output a notification indicating that preheating for X-ray irradiation is continuing via the indicator 128a provided at the holder 104 or the indicator 128 provided at the X-ray input apparatus 120. Thus, power consumption caused by a long-term preheating may be reduced.

In addition, when only the X-ray exposure signal is received from the X-ray input apparatus 120 with no X-ray exposure ready signal, the holder controller 151 may also output a notification indicating that only the X-ray exposure signal is output with no X-ray exposure ready signal via the indicator 128a provided at the holder 104 or the indicator 128 provided at the X-ray input apparatus 120. Thus, the user may recognize a network error and prevent erroneous X-ray irradiation.

However, the method of outputting a notification is not limited thereto and the notification may also be output via various other user interfaces such as the display device 111 provided in the X-ray imaging apparatus 100 in addition to the indicators 128 and 128a.

Meanwhile, when the X-ray input apparatus 120 and the holder 104 are spaced apart from each other at a distance exceeding a communicable range, signals cannot be exchanged therebetween after the pairing is completed due to characteristics of the short-range wireless communication. The input controller 121 of the X-ray input apparatus 120 may visually or audibly output a notification to prevent loss via the indicator 128 when the input controller 121 cannot communicate with the holder 104 for a predetermined time or more. Thus, loss or theft of the X-ray input apparatus 120 may be prevented.

When the holder controller 151 or the holder communicator 152 converts the signal received from the X-ray input apparatus 120 into a form that may be processed by the X-ray imaging apparatus 100, the holder controller 151 transmits the converted signal to the main controller 130 of the X-ray imaging apparatus 100.

The main controller 130 controls the overall operation of the X-ray imaging apparatus 100, particularly, controls the high voltage generator 160, the X-ray source 140, and the X-ray detector 400.

Upon receiving the X-ray exposure ready signal from the X-ray input apparatus 120, the main controller 130 may transmit a ready signal for preheating to the high voltage generator 160 and transmit a ready signal for X-rays detection to the X-ray detector 400.

The main controller 130 may include at least one memory for storing programs configured to perform operations described above and to be described below and at least one processor for executing the stored programs. In addition, the processors included in the main controller 130 may be classified according to an operation to be executed. For example, a process of controlling components used for X-ray irradiation and a processor of processing image signals received from the X-ray detector 400 may be provided. When the main controller 130 includes a plurality of processors and a plurality of memories, these processors and memories may be integrated in one chip or physically separated from each other.

The high voltage generator 160 starts preheating upon receiving the ready signal from the main controller 130 and outputs a signal indicating completion of a ready process to the main controller 130 when the preheating is completed.

The X-ray detector 400 may be a portable X-ray detector that is portable and connectable with the X-ray imaging apparatus 100 via a wireless communication network. The X-ray detector 400 may be included in the X-ray imaging apparatus 100 as a component or may be manufactured or sold separately from the X-ray imaging apparatus 100.

The main communicator 170 communicating with the X-ray detector 400 may include a communication module supporting at least one wireless communication methods such as Wireless LAN, Wi-Fi, Bluetooth, Zigbee, Wi-Fi Direct, Ultra Wideband (UWB), Infrared Data Association (IrDA), Bluetooth Low Energy (BLE), and Near Field Communication (NFC).

The X-ray detector 400 prepares for X-ray detection upon receiving the ready signal and outputs a signal indicating completion of a ready process to the main communicator 170 when preparation of X-ray detection is completed. Alternatively, transmission of the signal indicating completion of the ready process performed by the X-ray detector 400 may be omitted.

The main controller 130 may transmit the X-ray exposure signal to the high voltage generator 160 upon receiving the signal indicating completion of the ready process from the high voltage generator 160 and the X-ray detector 400 and the X-ray exposure signal from the holder controller 151. The high voltage generator 160, which receives the X-ray exposure signal as described above, applies a high voltage to the X-ray source 140 and the X-ray source 140 emits X-rays to the object.

The object refers to a target subjected to radiography to obtain internal images thereof as X-ray images. For example, the object may include organs such as liver, heart, womb, brain, breasts, and abdomen or blood vessels.

The X-ray source 140 may continuously emit X-rays to the object to acquire an X-ray video. A method of continuously emitting X-rays performed by the X-ray source 140 may include continuous exposure and pulse exposure.

In the case of the continuous exposure, the X-ray source 140 continuously emits a low dose of X-rays. In the case of the pulse exposure, the X-ray source 140 continuously emits a short pulse of X-rays.

The X-ray source 140 generates X-rays according to imaging parameters set by the main controller 130. The imaging parameters may also be referred to as exposure parameters. A process of automatically controlling the imaging parameters performed by the X-ray imaging apparatus 100 is referred to as Auto Exposure Control or Automatic Brightness Control, Automatic Dose Control, or Automatic Dose Rate Control.

The X-ray detector 400 detects X-rays emitted from the X-ray source 140 and acquires frame data by converting the detected X-rays into electrical signals. The frame data refers to each X-ray data acquired according to a frame rate of the X-ray imaging apparatus 100.

In addition, the X-ray detector 400 may have a two-dimensional array structure including a plurality of pixels and the X-ray detector 140 may acquire one piece of frame data by converting X-rays into electrical signals on the basis of pixel.

Also, the X-ray detector 400 may have any structure capable of detecting X-rays and converting the detected X-rays into electrical signals. For example, the X-ray detector 400 may be either a direct type in which X-rays are directly converted into electrical signals by using a photoconductor such as a-Se or an indirect type in which X-rays are converted into visible light and the visible light is converted into electrical signals by using a scintillator such as CSI.

The main controller 130 generates an X-ray image based on frame data output from the X-ray detector 400.

In addition, the main controller 130 may pre-process frame data before generating the X-ray image. For example, the main controller 130 may remove noise included in the frame data or correct errors between pixels of the X-ray detector 400.

Also, the main controller 130 may generate an X-ray video. As described above, when the X-ray source 140 emits X-rays at predetermined intervals, the X-ray detector 400 continuously outputs frame data by detecting X-rays at the time of X-ray irradiation. The main controller 130 may generate a plurality of X-ray images by using frame data continuously output from the X-ray detector 400 and generate the X-ray video by using the plurality of X-ray images.

The memory 180 stores data required to drive the X-ray imaging apparatus 100. For example, the memory 180 stores an operating system and applications necessary for driving the X-ray imaging apparatus 100.

The memory 180 may store data generated while the X-ray imaging apparatus 100 operates. For example, the memory 180 may store frame data output from the X-ray detector 400 or store the X-ray image or the X-ray video output from the main controller 130.

The memory 180 may include high-speed random access memory, magnetic disk, SRAM, DRAM, or ROM, without being limited thereto.

The memory 180 may be detachable from the X-ray imaging apparatus 100. For example, the memory 180 may include a compact flash (CF) card, a secure digital (SD) card, a smart media (SM) card, a multimedia card (MMC), or a memory stick, but the types of the memory 180 are not limited thereto.

The configuration of the X-ray imaging apparatus 100 and the configuration and operating principles of the mobile X-ray input apparatus 120 provided to output a control command to the X-ray imaging apparatus 100 have been described above.

The X-ray input apparatus 120 may be modified to have various other structures which will be described later. Hereinafter, modified embodiments will be described.

The X-ray input apparatus 120 may be charged in a wireless manner in a state of being mounted on the holder 104. Hereinafter, the X-ray input apparatus 120 capable of charging wirelessly according to an embodiment will be described with reference to the drawings.

Figure 13:
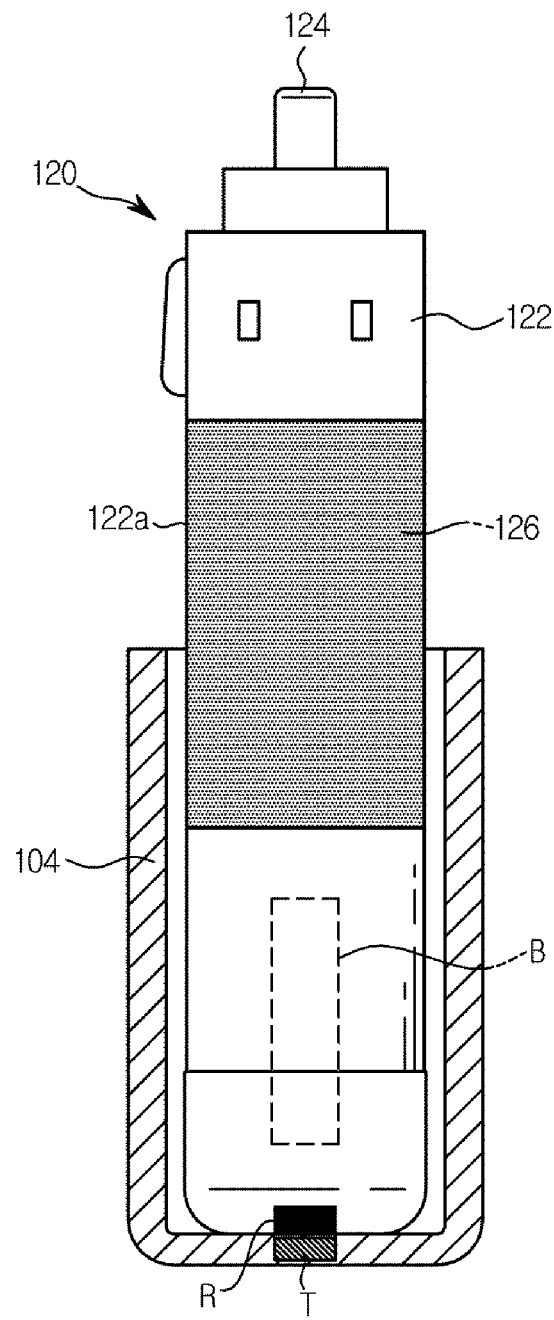
FIG. 13 is a view illustrating an appearance of a chargeable X-ray input apparatus.
Figure 14:
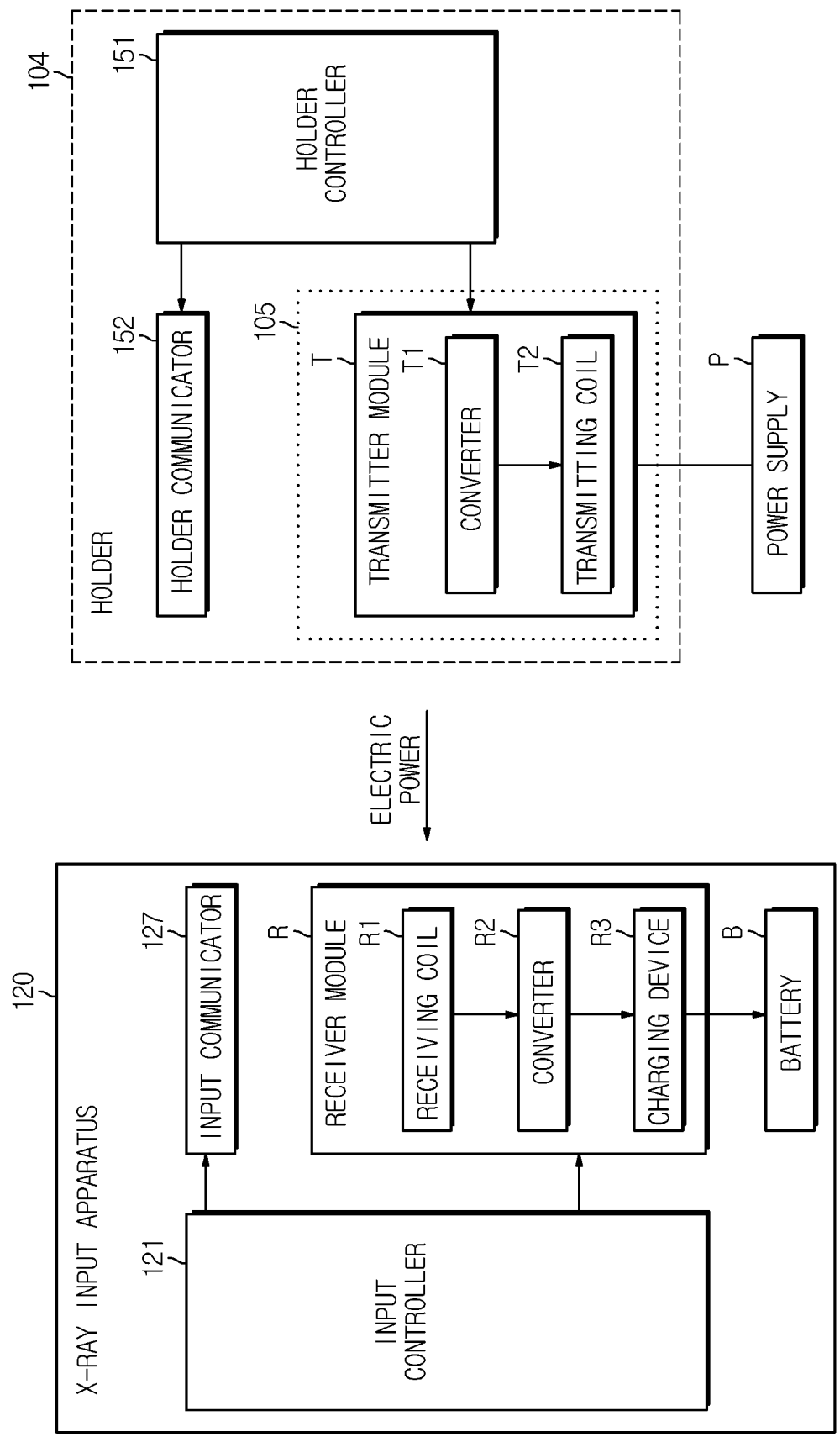
FIG. 14 is a control block diagram of a wirelessly chargeable X-ray input apparatus.

FIG. 13 is a view illustrating an appearance of a chargeable X-ray input apparatus. FIG. 14 is a control block diagram of a wirelessly chargeable X-ray input apparatus.

Referring to FIGS. 13 and 14, a charger 105 including a transmitter module T configured to transmit electrical energy to a battery B of the X-ray input apparatus 120 may be installed in the holder 104.

The X-ray input apparatus 120 may include a receiver module R located at a lower end of the body 122 and the battery B configured to receive power from the receiver module R and accumulate electrical energy for the operation of the X-ray input apparatus 120.

Hereinafter, these components will be described in more detail.

The transmitter module T includes a converter T1 connected to the power supply P and configured to convert a DC current supplied by the power supply P into an AC current and a transmitting coil T2 configured to form a magnetic field by the AC current.

The receiver module R may include a receiving coil R1 in which a current is induced by the magnetic field formed by the transmitting coil T2, a converter R2 configured to convert the induced AC current into a DC current, and a charging device R3 configured to convert the converted DC current into a chargeable form in the battery B.

When the X-ray input apparatus 120 is mounted on the holder 104, the input controller 121 of the X-ray input apparatus 120 outputs a charge request signal requesting charging of the battery to the holder 104. For example, the charge request signal may include ID information of the X-ray input apparatus 120. However, the charge request signal does not necessarily include a command that requests charging. When the battery of the X-ray input apparatus 120 is charged based on a signal received by the holder 104, the signal may also be referred to as the charge request signal.

The input controller 121 may output a signal by controlling a coil installed in the receiver module R or output a signal by controlling the input communicator 127 installed in the X-ray input apparatus 120 according to an embodiment.

Upon receiving the charge request signal, the holder controller 151 may control the transmitter module T to receive a power from the power supply P and the transmitter module T may supply electrical energy to the battery B of the X-ray input apparatus 120 by using the power received from the power supply P. Specifically, the transmitter module T may receive a DC power from the power supply P. When the converter T1 converts the DC current into an AC current, the converted AC current forms a magnetic field while flowing through the transmitting coil T2.

Meanwhile, any other methods in addition to the aforementioned magnetic induction method may also be applied to charge the X-ray input apparatus 120 wirelessly. For example, magnetic resonance or antenna methods may be used. Any method enabling wireless charging when the X-ray input apparatus 120 is mounted on the holder 104 may be used by locating coils and antennas in the X-ray input apparatus 120 and the holder 104. Detailed charging methods are not particularly limited.

As described above, when mounted on the holder 104, the mode of the X-ray input apparatus 120 may be switched to a sleeping mode. For example, upon determination that the X-ray input apparatus 120 is mounted on the holder 104 based on sensor values output from the position sensing device 123a provided in the X-ray input apparatus 120, the input controller 121 switches the mode of the X-ray input apparatus 120 to the sleeping mode and wireless charging may be performed by using the transmitter module T and the receiver module R.

When the X-ray input apparatus 120 is mounted on the holder 104 as described above, the mode is switched to the sleeping mode, thereby increasing battery charging efficiency of the X-ray input apparatus 120.

As described above, when the X-ray input apparatus 120 is mounted on the holder 104, the X-ray input apparatus 120 may be paired with the holder 104. When the X-ray input apparatus 120 is capable of charging wirelessly as the described embodiment, signals for the paring may be exchanged by using the receiving coil R1 and the transmitting coil T2 provided in the X-ray input apparatus 120 and the holder 104. In this case, the pairing request signal may be transmitted in a pulse form instead of the Bluetooth packet form.

For example, when the receiving coil R2 of the X-ray input apparatus 120 transmits a pairing request signal in a pulse form including ID information of the X-ray input apparatus 120, the transmitting coil T2 of the holder 104 receives the pairing request signal and the pairing may be completed. Alternatively, the pairing may also be completed after the holder 104 transmits a response signal to the X-ray input apparatus 120. Transmission of the response signal may also be performed by the coils or the Bluetooth communication module of the holder communicator 152.

After the pairing is completed, signals may be exchanged by using the input communicator 127 and the holder communicator 152 and wireless charging may be performed by using the transmitting coil T2 and the receiving coil R1 according to the afore-mentioned operations.

Also, when the X-ray input apparatus 120 is mounted on the holder 104 after the pairing has already been completed, wireless charging may be performed immediately.

Also, even when the X-ray input apparatus 120 is capable of charging wirelessly, the transmitting coil T2 and the receiving coil R1 may perform only a wireless charging operation while signals for pairing are exchanged by using the input communicator 127 and the holder communicator 152. In this case, when the X-ray input apparatus 120 is mounted on the holder 104, wireless charging may be performed regardless of performance of the pairing.

When the pairing of the X-ray input apparatus 120 with the holder 104 is completed, the X-ray input apparatus 120 may transmit information on a battery charge state to the holder 104 via the input communicator 127. The holder controller 151 may display the battery charge state of the X-ray input apparatus 120 via the indicator 128a.

The input controller 121 may control supply and cutoff of the power supplied to the battery B based on the battery charge state. For example, when charging of the battery B is completed, the supply of power may be cut off by controlling the receiver module R, thereby inhibiting overcharging.

Meanwhile, the receiver module R of the X-ray input apparatus 120 according to an embodiment may further include a charging terminal. In this regard, the charging terminal may be a charging terminal standardized to use the same USB port as mobile devices such as smartphones. In this case, the X-ray input apparatus 120 may be charged not only wirelessly but also using a separated cable.

As described above, in the case where the X-ray exposure command or the X-ray exposure ready command is received via the X-ray input apparatus 120, it is assumed that the touch sensing device 126 senses a touch of the operator. In order to obtain reliability of sensing results of the touch sensing device 126, the input controller 121 performs calibration control for the touch sensing device 126. Hereinafter, the calibration control will be described.

Figure 15:
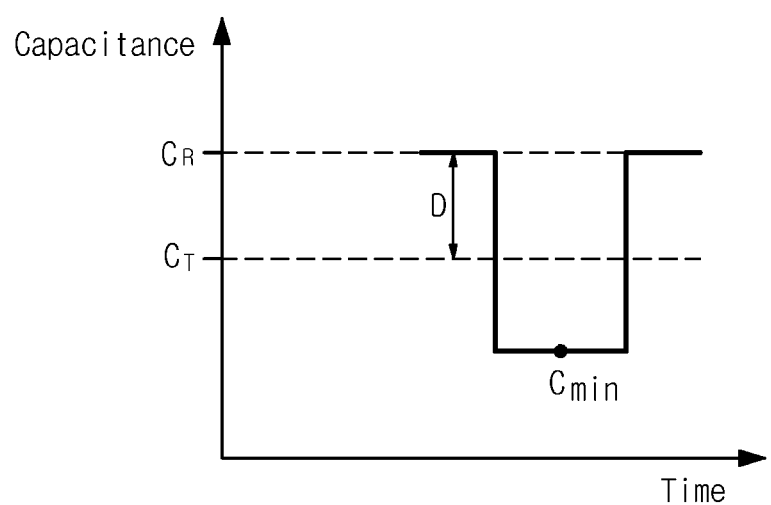
FIG. 15 is a graph illustrating capacitance threshold set by calibration control of an X-ray input apparatus according to an embodiment.

FIG. 15 is a graph illustrating capacitance threshold set by calibration control of an X-ray input apparatus according to an embodiment.

Calibration control for the touch sensing device 126 refers to determination of a capacitance threshold of the touch sensing device 126 based on a reference capacitance value of the touch sensing device 126. In this regard, the reference capacitance value refers to a capacitance value measured in the absence of external contact with the touch sensing device 126 and the capacitance threshold refers to a capacitance value that is used to recognize a capacitance change caused by an external stimulation as a touch stimulation of the operator. That is, when there is no external contact is made with the touch sensing device 126, the capacitance value may exceed the capacitance threshold. When an external contact is made with the touch sensing device 126, the capacitance value may be a capacitance threshold or less.

The reference capacitance value of the touch sensing device 126 may vary according to a surrounding environment such as temperature and humidity, touch sensitivity of the sensing device 126 may vary according to the surrounding environment. Thus, the capacitance threshold of the touch sensing device 126 needs to be periodically changed by calibration control performed by the touch sensing device 126. A process of re-setting the capacitance threshold based on the changed reference capacitance value of the touch sensing device 126 is referred to as calibration control for the touch sensing device 126.

Referring to the graph illustrated in FIG. 15, the input controller 121 may receive an output value of the touch sensing device 126 and use the received output value of the touch sensing device 126 as the reference capacitance value $C_R$. The output value of the touch sensing device 126 used as the reference capacitance value $C_R$ may be a value measured at the time of calibration control, a value measured at the time of inputting a calibration control command, or a value measured at a time therebetween.

A minimum value D of a capacitance change that may occur by a contact may be pre-stored and the input controller 121 may determine the capacitance threshold $C_T$ based on the reference capacitance value $C_R$ and the minimum value D of the capacitance change. For example, the input controller 121 may determine a value, which is smaller than the reference capacitance value $C_R$ by the minimum value D of the capacitance change, as the capacitance threshold $C_T$.

When calibration is normally performed as described above, the capacitance threshold $C_T$ may be determined a value between the reference capacitance value $C_R$ and a minimum capacitance value $C_{min}$ generated by the touch of the operator.

Next, a method of inputting a calibration control command to the touch sensing device 126 will be described.

Figure 16:
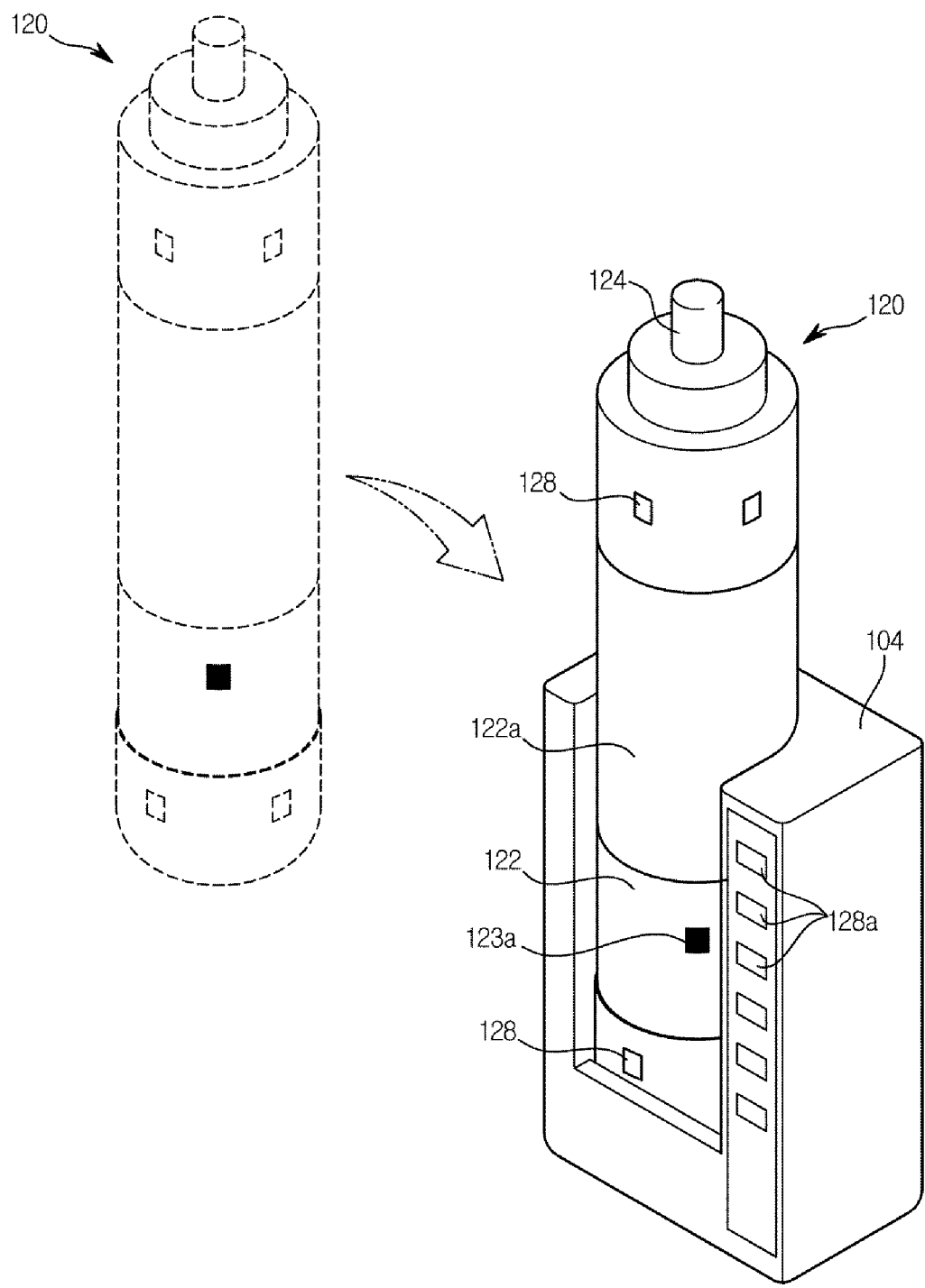
FIGS. 16 and 17 are views for describing a method of receiving a calibration control command by an X-ray input apparatus.
Figure 17:
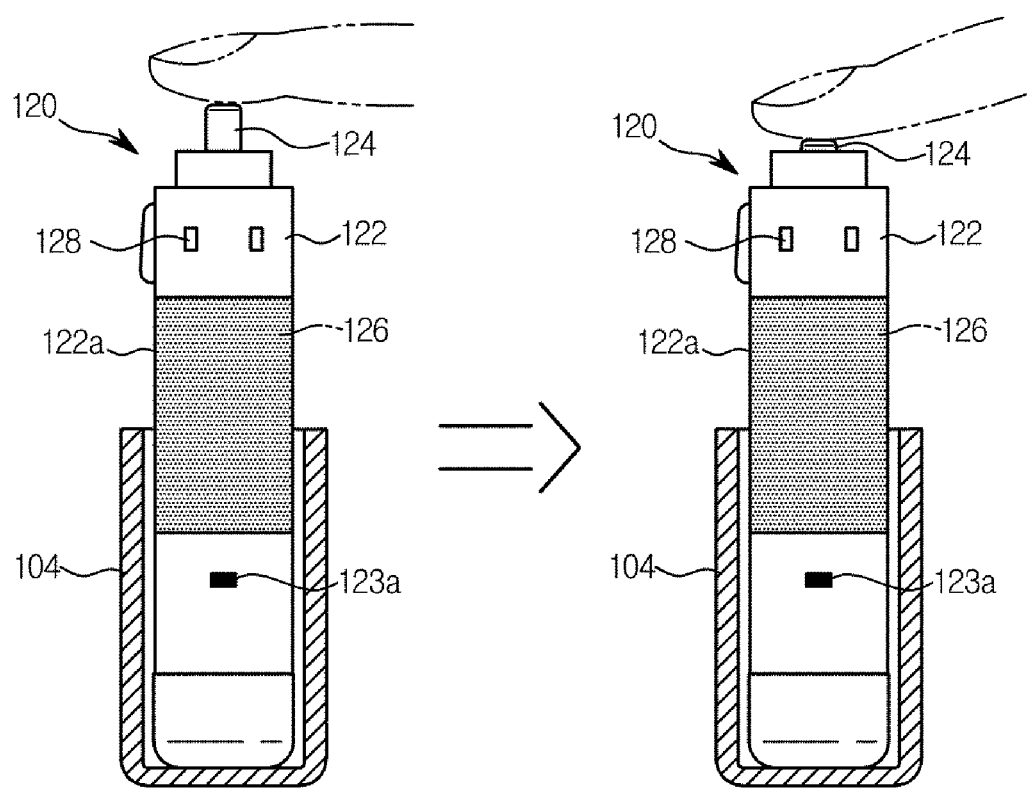

FIGS. 16 and 17 are views for describing a method of receiving a calibration control command by an X-ray input apparatus. Specifically, FIG. 16 illustrates a method of receiving input of a calibration control command as a method of recognizing that of the X-ray input apparatus 120 is mounted on the holder 104. FIG. 17 illustrates a method of receiving input of a calibration control command via the exposure button 124 provided at an upper portion of the body 122 of the X-ray input apparatus 120.

Referring to FIG. 16, when the X-ray input apparatus 120 is mounted on the holder 104, calibration control for the touch sensing device 126 may be performed. Specifically, the X-ray input apparatus 120 may determine whether or not the X-ray input apparatus 120 is mounted on the holder 104 based on sensor value information of the position sensing device 123a. As described above, the input controller 121 may pre-store a reference value indicating that the X-ray input apparatus 120 is mounted on the holder 104. When an output of the position sensing device 123a is included in the pre-stored reference value, the input controller 121 may determine that the X-ray input apparatus 120 is mounted on the holder 104.

Upon determination that the X-ray input apparatus 120 is mounted on the holder 104, the input controller 121 may automatically perform calibration control for the touch sensing device 126. The X-ray input apparatus 120 according to an embodiment may easily control calibration based on mounting information of the X-ray input apparatus 120 in the holder 104 although a separate command from the operator is not received.

Meanwhile, when the calibration control is performed in a state where a contact is made with the touch sensing device 126, the reference capacitance value $C_R$ is measured to be lower than an actual value. As a result, a calibration error in which the capacitance threshold $C_T$ is determined to be lower than a state where no contact is made with the touch sensing device 126 may occur. In some cases, the capacitance threshold $C_T$ may be determined as a value lower than the minimum capacitance value $C_{min}$.

However, by performing the calibration control only when the X-ray input apparatus 120 is mounted on the holder 104 as described above, a phenomenon that the capacitance threshold is set to an abnormally low value is caused by the calibration error may be prevented and accuracy of inputting the calibration control command may be improved in comparison with calibration control performed regardless of the mounting state of the X-ray input apparatus 120 in the holder 104.

In addition, it is possible to improve accuracy of calibration control by further using the output of the touch sensing device 126 in determining whether to perform calibration control. In this case, the input controller 121 may perform calibration control only when the X-ray input apparatus 120 is mounted on the holder 104 and an output of the touch sensing device 126 exceeds the capacitance threshold, i.e., when the operator does not grip the X-ray input apparatus 120.

Next, referring to FIG. 17, when the X-ray input apparatus 120 is mounted on the holder 104 and the exposure button 124 is located at a ready position, calibration control for the touch sensing device 126 may be performed.

That is, according to the embodiment, upon determination that the X-ray input apparatus 120 is mounted on the holder 104 based on the output of the position sensing device 123a and upon receiving input of the first signal from the exposure button 124, the input controller 121 determines that the calibration control command is input and performs a calibration control Furthermore, the input controller 121 may also determine whether or not the output of the touch sensing device 126 exceeds the capacitance threshold, i.e., whether or not the touch sensing device 126 receives a touch input. When the touch sensing device 126 does not receive the touch input, the input controller 121 may determine that the calibration control command is input.

When a case where the exposure button 124 of the X-ray input apparatus 120 mounted on the holder 104 is pressed is set as an input of the calibration control command as the described embodiment, a user's intention may more clearly reflected to perform unnecessary calibration.

Upon determination that the calibration control command is input, the input controller 121 may perform calibration control according to the operation described above.

Also, when an output value of the touch sensing device 126 is less than the capacitance threshold, the input controller 121 may determine that the X-ray exposure ready command or the X-ray exposure command is input based on the signal output from the exposure button 124.

Specifically, in the case where the output value of the touch sensing device 126 is less than the capacitance threshold, the input controller 121 may determine that the X-ray exposure ready command is input upon receiving the first signal from the exposure button 124 and that the X-ray exposure command is input upon receiving the second signal from the exposure button 124. The first signal may be a signal indicating that the exposure button 124 is pressed to the ready state or a signal indicating that a pressure of the first critical pressure or more to less than the second critical pressure is applied thereto. The second signal may be a signal indicating that the exposure button 124 is pressed to the exposure state or a signal indicating that a pressure of the second critical pressure or more is applied thereto.

In addition, the output of the position sensing device 123a may additionally be used. In this case, only when the output of the position sensing device 123a indicates that the X-ray input apparatus 120 is not mounted on the holder 104, it may be determined that the X-ray exposure ready command or the X-ray exposure command is input.

Hereinafter, various modified embodiments of the X-ray input apparatus will be described based on the afore-mentioned descriptions.

Next, the X-ray input apparatus 120 may further include a sensor configured to collect surrounding environment information.

Figure 18:
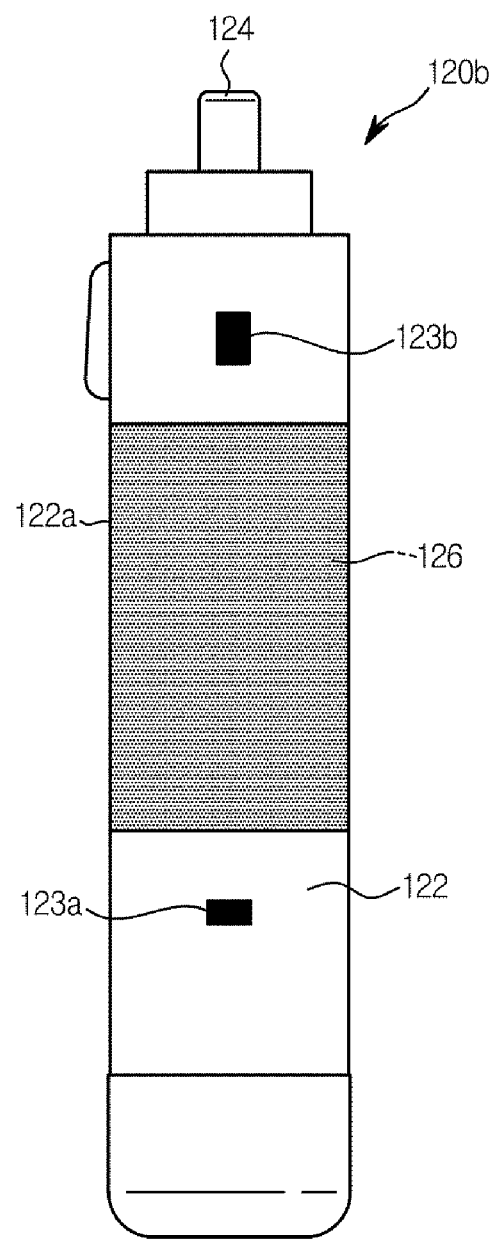
FIG. 18 is an X-ray input apparatus further including a sensor configured to acquire surrounding environment information.
Figure 19:
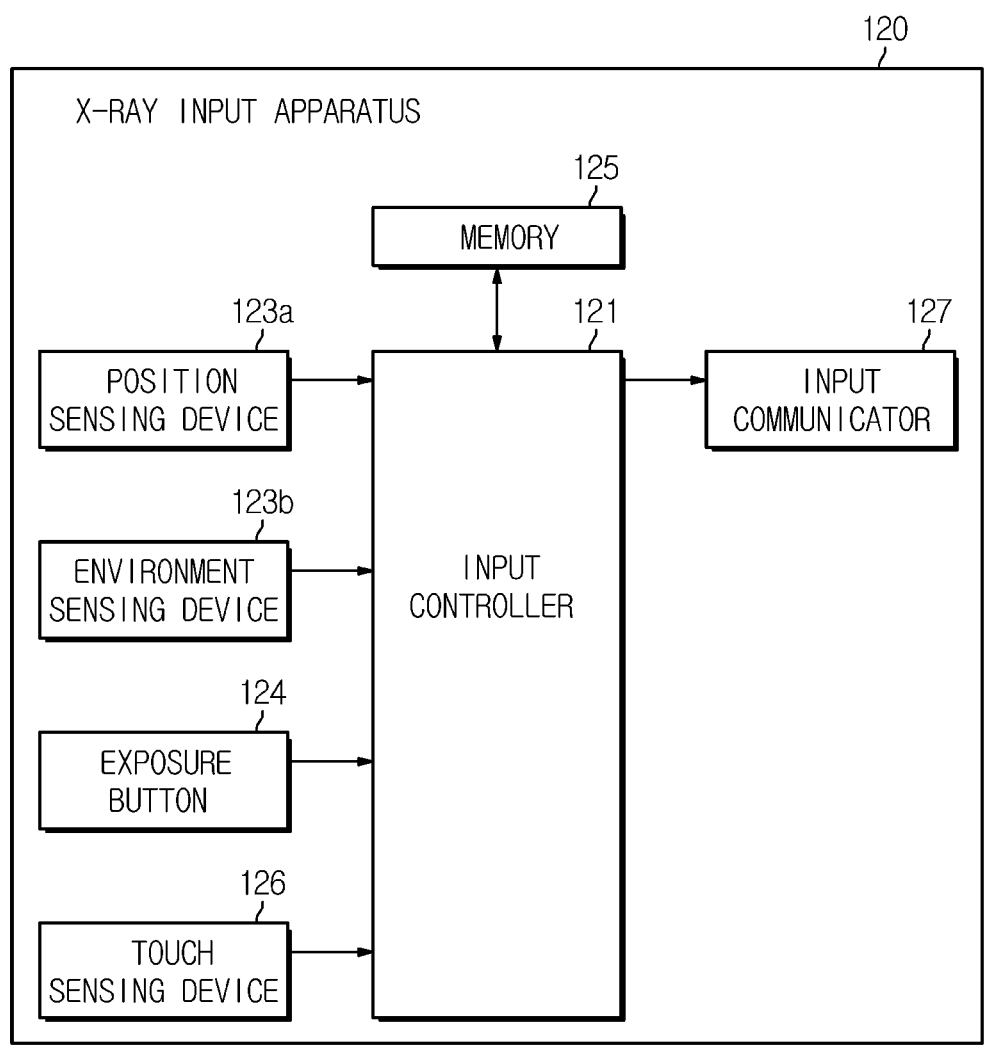
FIG. 19 is a control block diagram of the X-ray input apparatus illustrated in FIG. 18.
Figure 20:
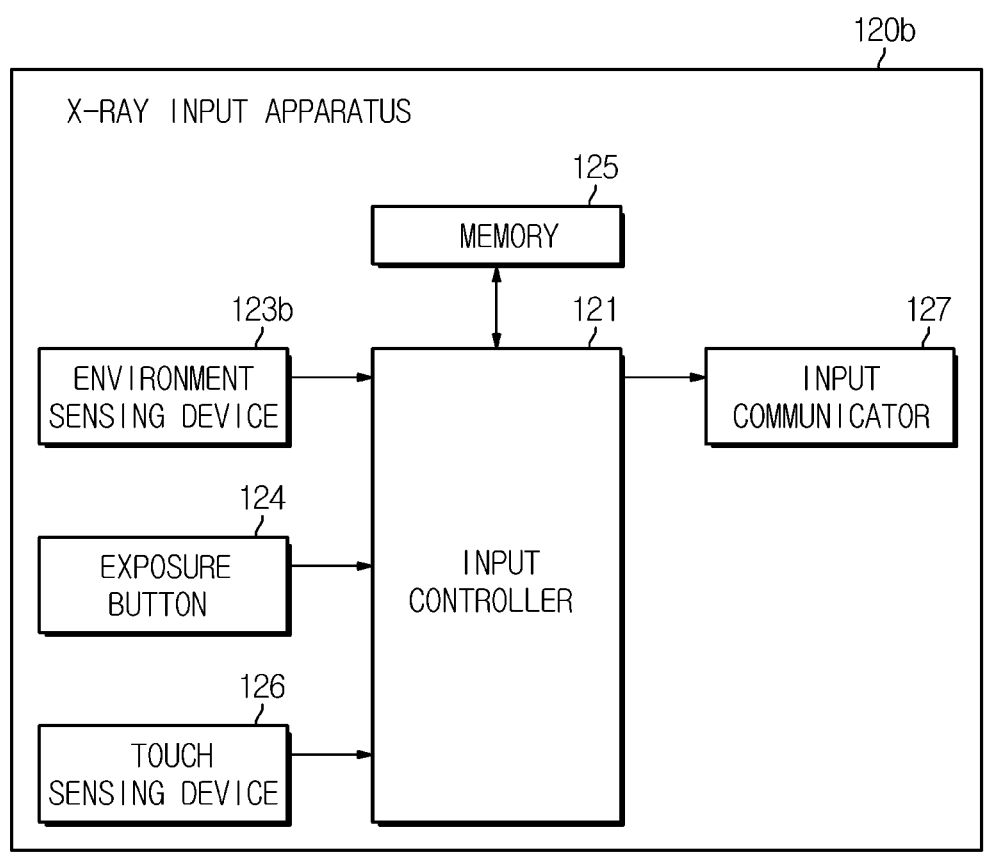
FIG. 20 is a control block diagram of an X-ray input apparatus from which the position sensing device is omitted.

FIG. 18 is an X-ray input apparatus further including a sensor configured to acquire surrounding environment information. FIG. 19 is a control block diagram of the X-ray input apparatus illustrated in FIG. 18. FIG. 20 is a control block diagram of an X-ray input apparatus from which the position sensing device is omitted.

Referring to FIGS. 18 and 19, the X-ray input apparatus 120 (120*b*) includes a position sensing device 123*a*, an environment sensing device 123*b*, an input communicator 127, an exposure button 124, a touch sensing device 126, a memory 125, and an input controller 121. Among these components of the X-ray input apparatus 120 according to the present embodiment, configurations and operations of the position sensing device 123*a*, the input communicator 127, the exposure button 124, the memory 125, and the touch sensing device 126 are as described above. Hereinafter, the embodiment will be described based on differences from those given above.

The environment sensing device 123*b* may be provided at the body 122 of the X-ray input apparatus 120 as illustrated in FIG. 18.

The environment sensing device 123 may include at least one of a temperature sensor and a humidity sensor. Thus, surrounding environment information acquired by the environment sensing device 123*b* may include temperature information and humidity information. The environment sensing device 123*b* may collect surrounding temperature information or humidity information in real time or at predetermined intervals and transmit the collected information to the input controller 121.

The input controller 121 may perform calibration control when the surrounding environment information received from the environment sensing device 123*b* satisfies calibration conditions.

For example, the input controller 121 may determine whether to perform calibration control based on output of the position sensing device 123*a* and the environment sensing device 123*b*. Particularly, the input controller 121 may determine whether or not the X-ray input apparatus 120 is mounted on the holder 104 based on the output of the position sensing device 123*a*. Upon determination that the X-ray input apparatus 120 is mounted on the holder 104, the input controller 121 may determine whether or not the calibration conditions are satisfied based on environment information obtained by the environment sensing device 123*b*. When the calibration conditions are satisfied, the input controller 121 may perform the calibration control.

For example, when the temperature information or humidity information included in the environment information is out of a set reference range, the calibration conditions may be satisfied. The reference range may be set to a fixed value or may also be reset whenever calibration is performed.

In the former case, it may be assumed that use environment of the X-ray input apparatus 120 is an environment in which a constant temperature and a constant humidity are maintained. In a situation where these constant environments cannot be maintained so, the temperature or the humidity is out of the reference range set to the fixed value, the capacitance threshold may be reset by performing calibration control. Also, even after the calibration control is performed, surrounding environment information may be collected periodically. When the collected temperature or humidity is within the reference range again, the capacitance threshold may be reset by performing calibration control again.

In the latter case, whenever the input controller 121 performs calibration control, temperature or humidity information at the time of calibration control may be stored and the reference range may be reset based on the stored temperature or humidity. When the surrounding environment information obtained after performing calibration control is out of the stored surrounding environment information by the reference range or more, it is determined that calibration conditions are satisfied and calibration control is performed again to reset the capacitance threshold. In this regard, the measured temperature or humidity information is also stored again.

According to the present embodiment, calibration control may be performed only when required by a change in the surrounding environment, thereby preventing unnecessary operations.

Also, the calibration control conditions may further include non-contact of the operator to improve accuracy of the calibration control. In this case, the input controller 121 may perform calibration control when the output of the environment sensing device 123*b* is out of a reference range and the output of the touch sensing device 126 exceeds the capacitance threshold.

Meanwhile, the order of determination of the mounting state in the holder 104 based on the output of the position sensing device 123*a* and determination of the satisfying state of calibration conditions based on the output of the environment sensing device 123*b* may also be changed.

In addition, the X-ray input apparatus 120 may perform calibration control based only on the output of the environment sensing device 123*b* regardless of the output of the position sensing device 123*a*. In this case, the input controller 121 may perform the calibration control when the output of the environment sensing device 123*b* satisfies calibration conditions regardless of the output of the position sensing device 123*a*.

In the case where the calibration control is performed regardless of the position of the X-ray input apparatus 120, the X-ray input apparatus 120 (120*b*) may not include the position sensing device 123*a* as illustrated in FIG. 20.

Meanwhile, the X-ray input apparatus may further include a button to receive a calibration control command. This will be described in more detail.

Figure 21:
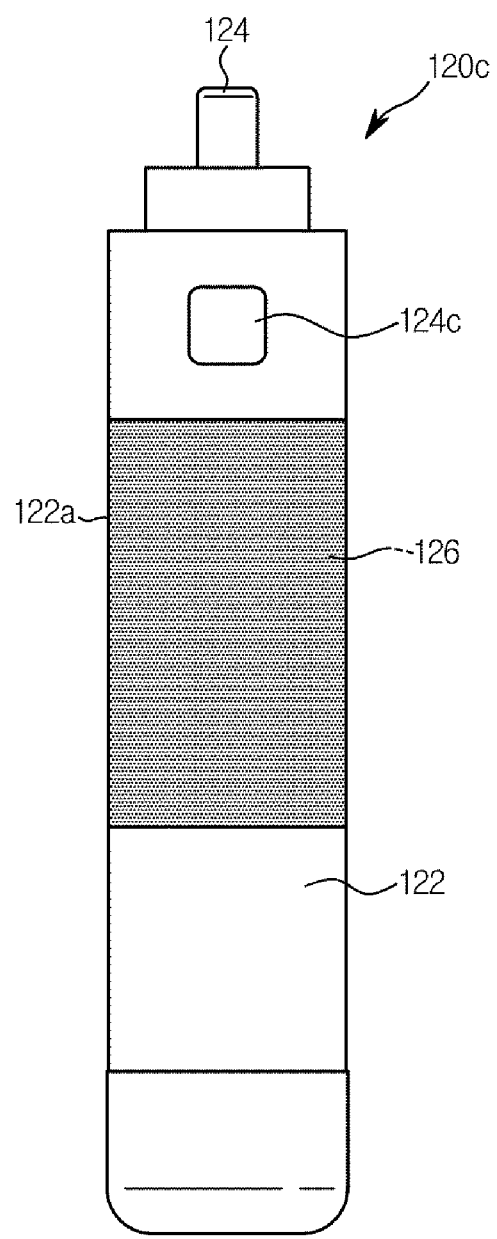
FIG. 21 is an X-ray input apparatus further including a calibration button.
Figure 22:
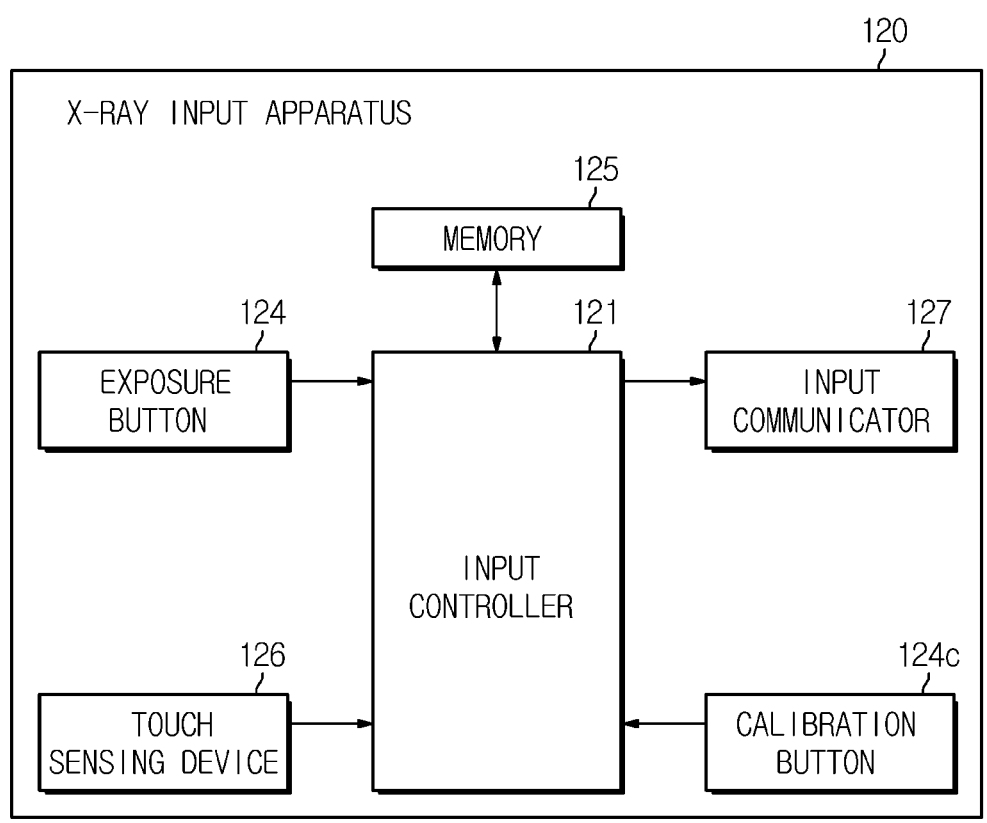
FIG. 22 is a control block diagram of the X-ray input apparatus of FIG. 21.
Figure 23:
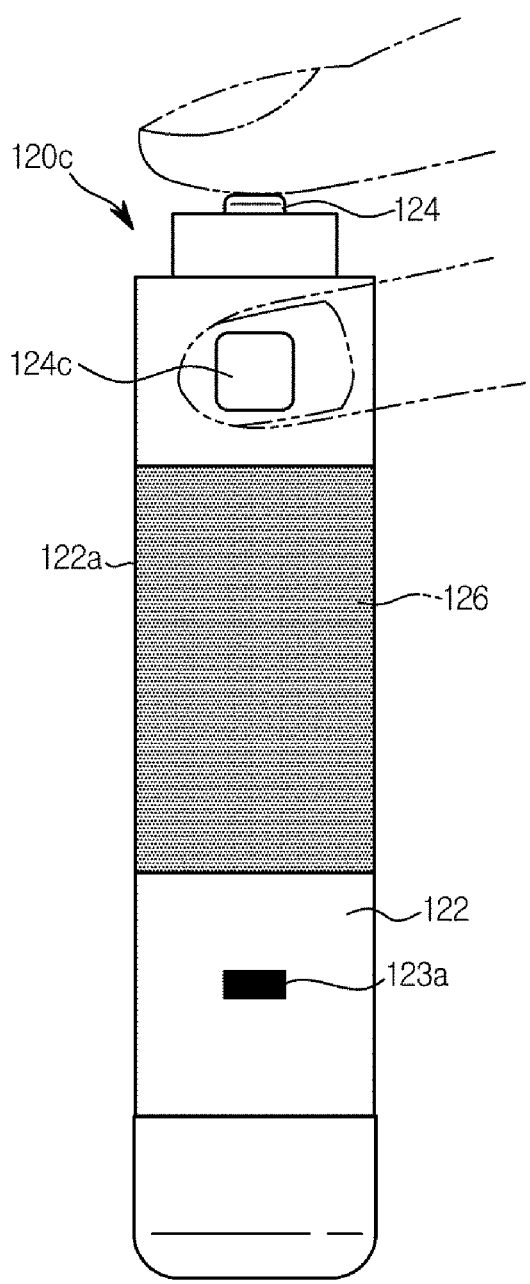
FIG. 23 is a view illustrating that an operator inputs a control command via the X-ray input apparatus of FIG. 21.

FIG. 21 is an X-ray input apparatus further including a calibration button. FIG. 22 is a control block diagram of the X-ray input apparatus of FIG. 21. FIG. 23 is a view illustrating that an operator inputs a control command via the X-ray input apparatus of FIG. 21.

The X-ray input apparatus 120 (120*c*) illustrated in FIGS. 21 and 22 includes a position sensing device 123*a*, a memory 125, an input communicator 127, an exposure button 124, a calibration button 124*c*, a touch sensing device 126, and an input controller 121. Among these components of the X-ray input apparatus 120, configurations and operations of the position sensing device 123*a*, the input communicator 127, the exposure button 124, the touch sensing device 126, and the input controller 121 are as described above. Hereinafter, the embodiment will be described based on differences from those given above.

The calibration button 124*c* may protrude from the surface of the body 122 of the X-ray input apparatus 120 as illustrated in FIG. 21. However, the calibration button 124*c* is not limited thereto and the calibration button 124*c* may also be implemented using a touch-type button.

As illustrated in FIG. 23, the operator may input a calibration control command by simultaneously pressing the calibration button 124c and the exposure button 124.

When the calibration button 124c is in contact or pressed, the calibration button 124c generates a third signal and transmits the third signal to the input controller 121. The third signal is a signal indicating that an input of the operator is received, i.e., the calibration button 124c is in contact or pressed.

When the third signal is received from the calibration button 124c and the first signal is received from the exposure button 124, the input controller 121 may determine that a calibration control command is input and perform calibration control. That is, when the exposure button 124 and the calibration button 124c are simultaneously pressed or in contact, the input controller 121 may determine that the calibration control command is input according to the present embodiment.

By performing calibration control in the case where signals are input by combining the outputs received from the exposure button 124 and the calibration button 124c, calibration may not be performed in an unintended situation. However, functions of the calibration button 124c are not limited thereto and additional functions may further be added to the calibration button 124c depending on the designer's intention.

Modified embodiments of the configuration and operation of the X-ray input apparatus have been described.

Hereinafter, a method of controlling an X-ray input apparatus according to an embodiment will be described. The embodiments of the X-ray input apparatus 120 and the X-ray imaging apparatus 100 described above may be applied to the method of controlling the X-ray input apparatus. Thus, descriptions given above with reference to FIGS. 1 to 23 may also be applied to the method of controlling the X-ray input apparatus which will be described later without any particular descriptions thereof.

Figure 24:
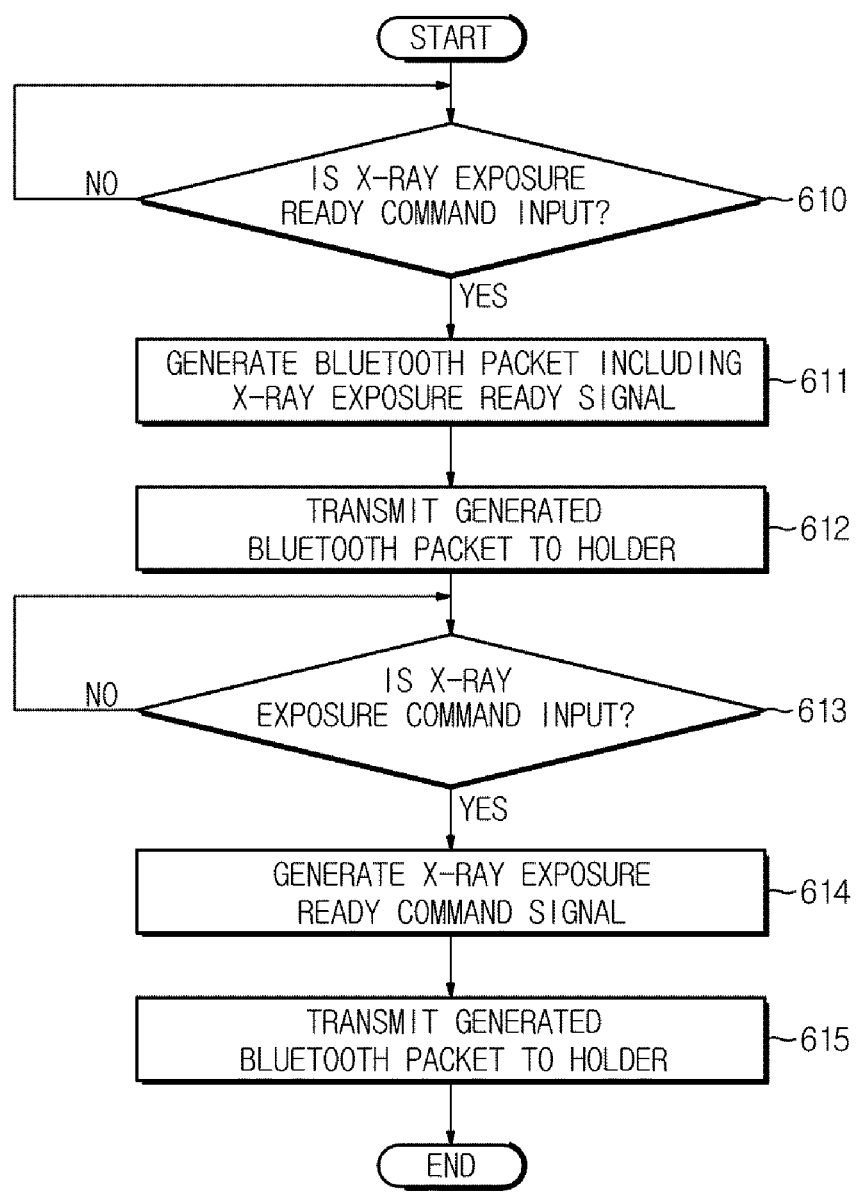
FIG. 24 is a flowchart for describing a method of controlling an X-ray input apparatus according to an embodiment.

FIG. 24 is a flowchart for describing a method of controlling an X-ray input apparatus according to an embodiment.

According to the method of controlling the X-ray input apparatus shown in FIG. 24, it is determined whether or not an X-ray exposure ready command is input by the user to the exposure button 124 provided at the X-ray input apparatus 120 (operation 610). For example, when the exposure button 124 is pressed by a pressure of the first critical pressure or more to less than the second critical pressure, it may be determined that the X-ray exposure ready command is input.

When the X-ray exposure ready command is input (Yes of operation 610), a Bluetooth packet including the X-ray exposure ready signal is generated (operation 611) and the generated Bluetooth packet is transmitted to the holder (operation 612). For example, the input controller 121 may generate the Bluetooth packet including the X-ray exposure ready signal and transmit the generated Bluetooth packet to the holder communicator 152 via the input communicator 127.

When the Bluetooth packet including the X-ray exposure ready signal is transmitted to the holder communicator 152, the holder controller 151 may convert the Bluetooth packet into a form that may be processed by the X-ray imaging apparatus 100 by decoding and transmit the converted signal to the main controller 130. When the X-ray exposure ready signal is transmitted, the main controller 130 may transmit a ready signal to the high voltage generator 160 and the X-ray detector 400. In this case, the high voltage generator 160 in which preheating is completed and the X-ray detector 400 in which X-ray detection is ready may transmit a signal indicating completion of a ready process to the main controller 130, respectively.

It is determined whether or not an X-ray exposure ready command is input by user (operation 613). For example, when the exposure button 124 is pressed by a pressure of the second critical pressure or more to less than the third critical pressure, it may be determined that the X-ray exposure command is input.

When the X-ray exposure command is input (Yes of operation 613), a Bluetooth packet including the X-ray exposure signal is generated (operation 614) and the generated Bluetooth packet is transmitted to the holder (operation 615). For example, the input controller 121 may generate the Bluetooth packet including the X-ray exposure signal and transmit the generated Bluetooth packet to the holder communicator 152 via the input communicator 127.

When the Bluetooth packet including the X-ray exposure signal is transmitted to the holder communicator 152, the holder controller 151 may convert the Bluetooth packet into a form that may be processed by the X-ray imaging apparatus 100 by decoding and transmit the converted signal to the main controller 130. When the X-ray exposure signal is transmitted and a signal indicating completion of a ready process is transmitted from the high voltage generator 160 and the X-ray detector 400, the main controller 130 may transmit the X-ray exposure signal to the high voltage generator 160.

In addition, the X-ray input apparatus 120 may add an On/Off signal of a lamp of the collimator 144 to the Bluetooth packet and transmit the Bluetooth packet to the holder 104.

Also, in the case where a packet is lost during a process of exchanging signals between the X-ray input apparatus 120 and the holder 104 due to a network error, or the like, a notification thereon may be output to prevent an erroneous emission of X-rays and reduce power consumption due to unnecessary preheating. Because exceptional processing caused by packet losses are as described above with reference to the embodiments of the X-ray imaging apparatus 100, detailed descriptions thereof will not be given.

Figure 25:
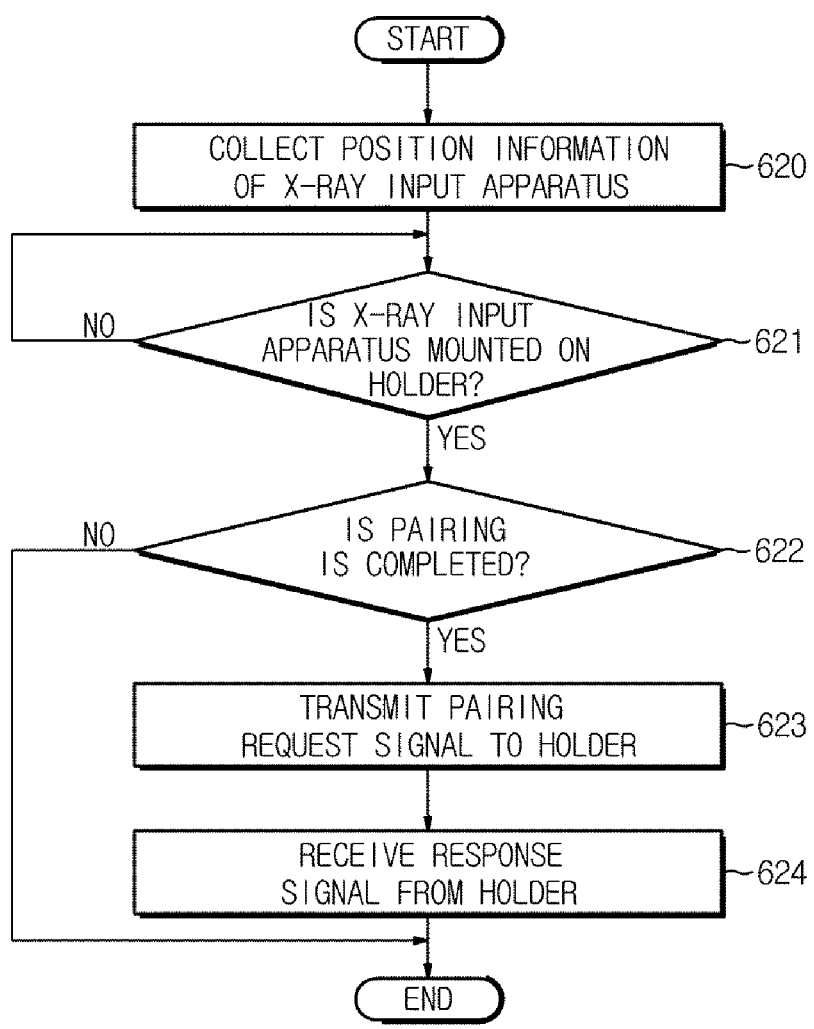
FIG. 25 is a flowchart for exemplarily describing a process of pairing an X-ray input apparatus with a holder in the method of controlling an X-ray input apparatus according to an embodiment.

FIG. 25 is a flowchart for exemplarily describing a process of pairing an X-ray input apparatus with a holder in the method of controlling an X-ray input apparatus according to an embodiment.

According to the method of controlling the X-ray input apparatus illustrated in FIG. 25, a position of the X-ray input apparatus is collected (operation 620). Position information of the X-ray input apparatus 120 may be collected by the position sensing device 123a.

The input controller 121 determines whether or not the X-ray input apparatus 120 is mounted on the holder 104 based on position information of the X-ray input apparatus (operation 621). Particularly, the input controller 121 may compare an output value of the position sensing device 123a with a pre-stored reference value. When the output value of the position sensing device 123a is equal to or greater than the reference value or equal to or less than the reference value, the input controller 121 may determine that the X-ray input apparatus 120 is mounted on the holder 104. The pre-stored reference value may vary according to types of the position sensing device 123a.

Upon determination that the X-ray input apparatus 120 is mounted on the holder 104 (Yes of operation 621), it is determined whether or not the X-ray input apparatus 120 and the holder 104 are in a paired state currently (operation 622). When the X-ray input apparatus 120 and the holder 104 are not in a paired state (No of operation 622), a pairing request signal is transmitted to the holder 104 (operation 623). For example, when the X-ray input apparatus 120 communicates with the holder 104 by a Bluetooth communication method, the input communicator 127 may generate a Bluetooth packet including ID information of the X-ray input apparatus 120 and transmit the Bluetooth packet to the holder 104.

The holder 104 that has received the pairing request signal may transmit a response signal to the input communicator 127. When the input communicator 127 receives the response signal from the holder 104 (operation 624), pairing of the X-ray input apparatus 120 with the holder 104 is completed, and thus a connection state in which signals may be exchanged with each other is established.

Although the pairing is established when the X-ray input apparatus 120 is mounted on the holder 104 as illustrated in the flowchart, pairing may also be established when a pairing command is input by user via a pairing button 129 provided at the body 122 of the X-ray input apparatus 120.

When the pairing of the holder 104 with the X-ray input apparatus 120 is completed, the X-ray input apparatus 120 may transmit a Bluetooth packet including the X-ray exposure ready signal and the X-ray exposure signal to the holder 104.

Meanwhile, when a distance between the holder 104 and the X-ray input apparatus 120 is maintained beyond a communicable range for a reference time or more after the pairing of the holder 104 with the X-ray input apparatus 120 is completed, i.e., when the X-ray input apparatus 120 is not communicable with the holder 104 for the reference time or more, the input controller 120 may visually or audibly output a notification to prevent loss or theft. When an audible notification is output, the notification may be output via a speaker provided in the X-ray input apparatus 120. When a visible notification is output, the notification may be output via the indicator 128 provided at the X-ray input apparatus 120.

Figure 26:
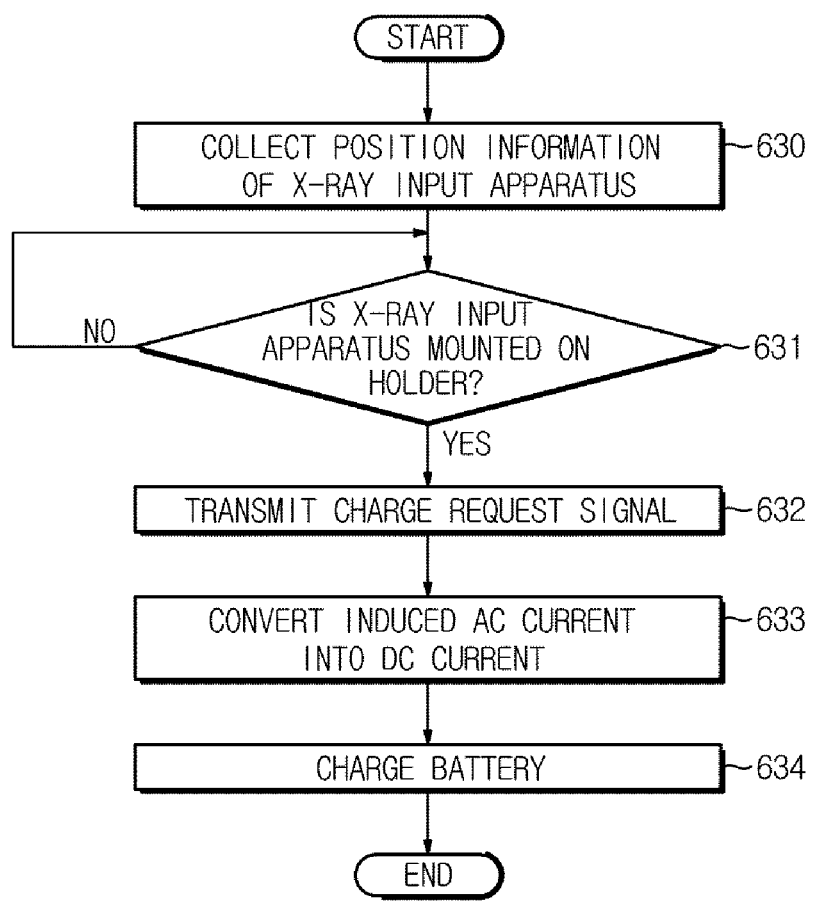
FIG. 26 is a flowchart for describing a method of wirelessly charging an X-ray input apparatus in a holder in the method of controlling an X-ray input apparatus according to an embodiment.

FIG. 26 is a flowchart for describing a method of wirelessly charging an X-ray input apparatus in a holder in the method of controlling an X-ray input apparatus according to an embodiment. In the method of controlling the X-ray input apparatus according to the present embodiment, the X-ray input apparatus 120 described above with reference to FIGS. 13 and 14 may be used.

According to the method of controlling the X-ray input apparatus shown in FIG. 26, position information of the X-ray input apparatus is collected (operation 630). The position information of the X-ray input apparatus 120 may be collected by the position sensing device 123a.

The input controller 121 may determine whether or not the X-ray input apparatus 120 is mounted on the holder 104 based on position information of the X-ray input apparatus (operation 631).

Upon determination that the X-ray input apparatus 120 is mounted on the holder 104 (Yes of operation 631), the input controller 121 transmits a charge request signal requesting battery charging to the holder 104 (operation 632). In this case, the input controller 121 may output the signal by a method of controlling a coil installed in the receiver module R. According to an embodiment, the signal may be output by a method of controlling the input communicator 127 installed in the X-ray input apparatus 120.

When the charge request signal is received, the holder controller 151 may turn on the power supplied to the transmitter module T to transmit electrical energy to the battery B of the X-ray input apparatus 120. For example, the transmitter module T receives a DC current from the power supply P. When the converter $C_T$ converts the DC current into an AC current, the converted AC current may form a magnetic field while flowing through the transmitting coil T2.

When a current is induced in the receiving coil R1 by the magnetic field formed by the transmitting coil T2, the converter R2 of the receiver module R converts the induced current into a DC current (operation 633).

The charging device R3 converts the DC current into a form that may be charged to the battery B to charge the battery B (operation 634).

When the X-ray input apparatus 120 is mounted on the holder 104 as described above, the input controller 121 may switch the X-ray input apparatus 120 to the sleeping mode. When the mode of the X-ray input apparatus 120 is switched to the sleeping mode, battery charging efficiency may be improved.

Meanwhile, when the X-ray input apparatus 120 is not paired with the holder 104 after the X-ray input apparatus 120 is mounted on the holder 104, the pairing may be performed according to the afore-mentioned process and wireless charging may be performed after completion of the pairing. Alternatively, wireless charging may also be performed regardless of the paring.

When the X-ray input apparatus 120 is paired with the holder 104, coils of the transmitter module T and the receiver module R may be used to transmit/receive signals instead of the input communicator 127.

When the X-ray input apparatus 120 has been paired with the holder 104, the input controller 121 of the X-ray input apparatus 120 may transmit information on a charging state of the battery B to the holder 104 via the input communicator 127. The holder controller 151 may display the battery charge status of the X-ray input apparatus 120 via the indicator 128a.

In addition, the holder controller 151 may control supply and cutoff of the power supplied from the power supply P based on the battery charge status. For example, when charging of the battery B is completed, the power supplied from the power supply P may be cutoff to prevent overcharging.

Meanwhile, when the X-ray input apparatus 120 is mounted on the holder 104, the calibration control of the touch sensing device 126 may be performed. In this case, the operations may be performed in the order of pairing, calibration control, and wireless charging or in the order of pairing, wireless charging, and calibration control.

According to an embodiment, the pairing button 129 may be separately located and pairing may be performed when the pairing command is input by user via the pairing button 129. In this case, when the X-ray input apparatus 120 is mounted on the holder 104, the calibration control may be performed and wireless charging may be performed upon completion of the calibration control.

Also, according to an embodiment, when the X-ray input apparatus 120 is mounted on the holder 104 and the exposure button 124 is pressed, the calibration control may be performed. In this case, wireless charging may be performed when the X-ray input apparatus 120 is mounted on the holder 104.

As is apparent from the above description, the following effects may be obtained according to the X-ray input apparatus and the method of controlling the same according to embodiments of the present disclosure.

First, because calibration of the touch sensing device is performed when the X-ray input apparatus is mounted on the holder, accuracy of the calibration operation may be increased and calibration may be automatically performed with no particular manipulation of the operator.

Also, because the calibration control command of the touch sensing device is input via a plurality of input devices provided at the X-ray input apparatus, accuracy of the calibration may be increased.

Furthermore, because the calibration control of the touch sensing device is performed based on information on surrounding environment of the X-ray input apparatus, the calibration control for the touch sensing device may be automatically performed with no particular manipulation of the operator.

Furthermore, Because the X-ray input apparatus is charged when the X-ray input apparatus is mounted on the holder, inconvenience of periodically replacing the battery of the X-ray input apparatus may be removed.

Furthermore, by simplifying a pairing process between the X-ray input apparatus and the holder, a process of setting the devices may become more convenient.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An X-ray input apparatus for controlling an X-ray imaging apparatus including a holder with a holder controller and a holder communicator, the X-ray input apparatus comprising:
   an indicator;
   a body mountable on the holder;
   an exposure button provided at an upper portion of the body and including a first stage and a second stage;
   an input communicator configured to communicate with the holder via a Bluetooth communication network; and
   an input controller configured to control the input communicator to:
      generate a Bluetooth packet including an X-ray exposure ready signal and transmit the generated Bluetooth packet to the holder via the Bluetooth communication network when the first stage of the exposure button is actuated, and
      generate a Bluetooth packet including an X-ray exposure signal, and transmit the generated Bluetooth packet to the holder via the Bluetooth communication network, when the second stage of the exposure button is actuated,
   wherein the input controller is further configured to control the indicator to output a notification generated by the holder when the Bluetooth packet including the X-ray exposure signal is received before the Bluetooth packet including the X-ray exposure ready signal is received.

2. The X-ray input apparatus of claim 1, wherein the input controller is further configured to control the input communicator to generate a pairing Bluetooth packet including identification information of the X-ray input apparatus and transmit the generated pairing Bluetooth packet to the holder for pairing with the holder.

3. The X-ray input apparatus of claim 1, wherein the input controller is further configured to generate an anti-theft notification when a distance between the holder and the X-ray input apparatus is maintained beyond a communicable range for at least a predetermined amount of time.

4. The X-ray input apparatus of claim 1, further comprising:
   a receiver module including a receiving coil configured to interact with a transmitting coil of the holder via a magnetic field to induce an AC current in the receiving coil, and a converter configured to convert the induced AC current to a DC current; and
   a battery configured to be charged by the DC current.

5. The X-ray input apparatus of claim 4, wherein the input controller is further configured to control the input communicator to generate a battery Bluetooth packet including information on a charge status of the battery and transmits the generated battery Bluetooth packet to the holder.

6. The X-ray input apparatus of claim 4, wherein the input controller is further configured to transmit a battery charge request signal to the holder via at least one of the receiving coil and the input communicator when the body is mounted on the holder.

7. The X-ray input apparatus of claim 4, wherein the input controller is further configured to transmit a pulse signal including identification information of the X-ray input apparatus to the transmitting coil of the holder via the receiving coil for pairing the X-ray input apparatus with the holder.

8. The X-ray input apparatus of claim 1, wherein the input controller is further configured to switch an operation mode of the X-ray input apparatus to a sleeping mode when the body is mounted on the holder.

9. An X-ray imaging apparatus comprising:
   an X-ray source configured to generate X-rays and emit the generated X-rays;
   a high voltage generator configured to supply a high voltage to the X-ray source;
   an X-ray input apparatus configured to generate a Bluetooth packet including at least one of an X-ray exposure ready signal and an X-ray exposure signal when an X-ray exposure ready command or an X-ray exposure command is input by a user; and
   a holder, including a holder controller and a holder communicator, on which the X-ray input apparatus is mounted and configured to communicate with the X-ray input apparatus via a Bluetooth communication network,
   wherein the holder is further configured to output a notification when the Bluetooth packet including the X-ray exposure signal is received before the Bluetooth packet including the X-ray exposure ready signal is received.

10. The X-ray imaging apparatus of claim 9, wherein the X-ray input apparatus is further configured to generate a distance Bluetooth packet including an anti-theft notification, and transmit the generated distance Bluetooth packet to the holder when a distance between the holder and the X-ray input apparatus is maintained beyond a communicable range for at least a predetermined amount of time.

11. The X-ray imaging apparatus of claim 9, further comprising:
   a transmitting coil provided at the holder and configured to form a magnetic field;
   a receiving coil configured to interact with the transmitting coil via the magnetic field to induce a current in the receiving coil; and
   a battery configured to be charged by the current induced in the receiving coil and configured to supply power to the X-ray input apparatus.

12. The X-ray imaging apparatus of claim 11, wherein the X-ray input apparatus is further configured to generate a battery Bluetooth packet including information on a charge status of the battery, and transmit the generated battery Bluetooth packet to the holder.

13. The X-ray imaging apparatus of claim 11, wherein the X-ray input apparatus is further configured to transmit a pulse signal comprising identification information of the X-ray input apparatus to the transmitting coil of the holder via the receiving coil for pairing the X-ray input apparatus with the holder.

14. The X-ray imaging apparatus of claim 13, wherein the X-ray input apparatus communicates with the holder via the Bluetooth communication network after completion of the pairing of the X-ray input apparatus with the holder.

15. The X-ray imaging apparatus of claim 9, wherein the holder is further configured to generate a notification when the X-ray exposure signal is not received via the generated Bluetooth packet within a predetermined reference time after receiving the X-ray exposure ready signal.

16. A method of controlling an X-ray input apparatus provided to be mounted on a holder of an X-ray imaging apparatus including a holder controller and a holder communicator, the method comprising:

determining whether at least one of a first stage and a second stage of an exposure button provided on the X-ray input apparatus is actuated by a user;

generating a Bluetooth packet including an X-ray exposure ready signal, when the determining indicates the first stage of the exposure button is actuated; and generating a Bluetooth packet including an X-ray exposure signal, when the determining indicates the second stage of the exposure button is actuated;

transmitting the generated Bluetooth packet including the X-ray exposure ready signal or the generated Bluetooth packet including the X-ray exposure signal to the holder; and outputting a notification generated by the holder when the Bluetooth packet including the X-ray exposure signal is received before the Bluetooth packet including the X-ray exposure ready signal is received.

17. The method of claim 16, further comprising generating a pairing Bluetooth packet including identification information of the X-ray input apparatus and transmitting the generated pairing Bluetooth packet to the holder for pairing the X-ray input apparatus with the holder when the X-ray input apparatus is not paired with the holder.

18. The method of claim 16, further comprising generating an anti-theft notification when a distance between the holder and the X-ray input apparatus is maintained beyond a communicable range for at least a predetermined amount of time.

19. The method of claim 16, further comprising inducing a current in a receiving coil of the holder by a magnetic field formed by a transmitting coil of the holder.

* * * * *